US008114841B2

(12) United States Patent
Lynch et al.

(10) Patent No.: US 8,114,841 B2
(45) Date of Patent: Feb. 14, 2012

(54) MAXILLOFACIAL BONE AUGMENTATION USING RHPDGF-BB AND A BIOCOMPATIBLE MATRIX

(75) Inventors: Samuel E. Lynch, Franklin, TN (US); Myron Nevins, Swampscott, MA (US); Massimo Simion, Milan (IT)

(73) Assignee: BioMimetic Therapeutics, Inc., Franklin, TN (US)

( * ) Notice: Subject to any disclaimer, the term of this patent is extended or adjusted under 35 U.S.C. 154(b) by 1388 days.

(21) Appl. No.: 11/601,376

(22) Filed: Nov. 17, 2006

(65) Prior Publication Data

US 2007/0129807 A1    Jun. 7, 2007

Related U.S. Application Data

(63) Continuation-in-part of application No. 11/159,533, filed on Jun. 23, 2005, now Pat. No. 7,473,678, which is a continuation-in-part of application No. 10/965,319, filed on Oct. 14, 2004, now abandoned.

(60) Provisional application No. 60/738,076, filed on Nov. 17, 2005.

(51) Int. Cl.
*A61K 38/18* (2006.01)

(52) U.S. Cl. .......... 514/8.2; 514/7.6; 424/489; 424/484; 424/499

(58) Field of Classification Search ........................ None
See application file for complete search history.

(56) References Cited

U.S. PATENT DOCUMENTS

| | | | |
|---|---|---|---|
| 3,943,072 A | 3/1976 | Thomson et al. | |
| 4,795,467 A * | 1/1989 | Piez et al. ..................... | 424/423 |
| 4,845,075 A | 7/1989 | Murray et al. | |
| 4,861,757 A | 8/1989 | Antoniades et al. | |
| 4,874,746 A | 10/1989 | Antoniades et al. | |
| RE33,161 E | 2/1990 | Brown et al. | |
| 4,904,259 A | 2/1990 | Itay | |
| 4,963,145 A | 10/1990 | Takagi et al. | |
| 4,975,526 A | 12/1990 | Kuberasampath et al. | |
| 5,011,910 A | 4/1991 | Marshall et al. | |
| 5,013,649 A | 5/1991 | Wang et al. | |
| 5,019,559 A | 5/1991 | Antoniades et al. | |
| 5,034,375 A | 7/1991 | Antoniades et al. | |
| 5,035,887 A | 7/1991 | Antoniades et al. | |
| 5,045,633 A | 9/1991 | Murray et al. | |
| 5,053,212 A | 10/1991 | Constantz et al. | |
| 5,106,748 A | 4/1992 | Wozney et al. | |
| 5,108,922 A | 4/1992 | Wang et al. | |
| 5,112,354 A | 5/1992 | Sires | |
| 5,116,738 A | 5/1992 | Wang et al. | |
| 5,124,316 A | 6/1992 | Antoniades et al. | |
| 5,128,321 A | 7/1992 | Murray et al. | |
| 5,129,905 A | 7/1992 | Constantz | |
| 5,141,905 A | 8/1992 | Rosen et al. | |
| 5,149,691 A | 9/1992 | Rutherford | |
| 5,165,938 A | 11/1992 | Knighton | |
| 5,187,076 A | 2/1993 | Wozney et al. | |
| 5,187,263 A | 2/1993 | Murray et al. | |
| 5,219,576 A | 6/1993 | Chu et al. | |
| 5,219,759 A | 6/1993 | Heldin et al. | |
| 5,270,300 A | 12/1993 | Hunziker | |
| 5,290,708 A | 3/1994 | Ashihara et al. | |
| 5,338,772 A | 8/1994 | Bauer et al. | |
| 5,376,636 A | 12/1994 | Rutherford et al. | |
| 5,457,093 A | 10/1995 | Cini et al. | |
| 5,460,962 A | 10/1995 | Kemp | |
| 5,516,896 A | 5/1996 | Murray et al. | |
| 5,518,680 A | 5/1996 | Cima et al. | |
| 5,531,794 A | 7/1996 | Takagi et al. | |
| 5,533,836 A | 7/1996 | Moore | |
| 5,549,123 A | 8/1996 | Okuyama et al. | |
| 5,599,558 A | 2/1997 | Gordinier et al. | |
| 5,629,191 A | 5/1997 | Cahn | |
| 5,635,372 A | 6/1997 | Celeste et al. | |
| 5,650,176 A | 7/1997 | Lee et al. | |
| 5,747,273 A | 5/1998 | Khosravi et al. | |
| 5,759,815 A | 6/1998 | Charette et al. | |
| 5,783,217 A | 7/1998 | Lee et al. | |
| 5,804,176 A | 9/1998 | Grotendorst | |
| 5,837,258 A | 11/1998 | Grotendorst | |

(Continued)

FOREIGN PATENT DOCUMENTS

EP        0 289 584 B1     11/1988

(Continued)

OTHER PUBLICATIONS

"SynthoGraft Pure Phase Beta-Tricalcium Phosphate: The Next Generation of Regeneration" SynthoGraft Product Information Brochure, 6 pages (no date) retrieved Apr. 12, 2011.*
Lioubavina-Hack, Natalia et al., "Effects of Bio-Oss with or without platelet-derived growth factor on bone formation by "guided tissue regeneration:" a pilot study in rats," *Journal of Clinical Periodontology*, vol. 32, Dec. 2005, pp. 1254-1260.
Sarment, David P. et al., "Effect of rhPDGF-BB on bone turnover during periodontal repair," *Journal of Clinical Periodontology*, vol. 33, Feb. 2006, pp. 135-140.
International Search Report and Written Opinion issued for PCT/US2006/044766 mailed Dec. 7, 2007.

(Continued)

*Primary Examiner* — Allison Ford
(74) *Attorney, Agent, or Firm* — Earl M. Douglas; Michael D. Ruse, Jr.

(57) ABSTRACT

The present invention provides effective new methods and materials for maxillofacial bone augmentation, particularly alveolar ridge augmentation, that are free of problems associated with prior art methods. In one embodiment, these materials include human recombinant platelet derived growth factor (rhPDGF-BB) and a biocompatible matrix. In another embodiment, these materials include rhPDGF-BB, a deproteinized bone block or calcium phosphate, and a bioresorbable membrane. The use of these materials in the present method is effective in regenerating maxillofacial bones and facilitating achievement of stable osseointegrated implants. The mandible and maxilla are preferred bones for augmentation, and enhancement of the alveolar ridge is a preferred embodiment of the present invention.

40 Claims, 3 Drawing Sheets

U.S. PATENT DOCUMENTS

| | | |
|---|---|---|
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,030,636 A | 2/2000 | Randolph et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson et al. |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 | 2/2009 | Hart et al. |
| 7,597,883 B2 | 10/2009 | Hart et al. |
| 7,799,754 B2 | 9/2010 | Hart et al. |
| 7,943,573 B2 | 5/2011 | Lynch et al. |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0049328 A1 | 3/2003 | Dalal et al. |
| 2003/0055511 A1 | 3/2003 | Schryver et al. |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1 | 1/2004 | King et al. |
| 2004/0014727 A1* | 1/2004 | Garrett .................. 514/102 |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |
| 2005/0107887 A1 | 5/2005 | Knothe Tate et al. |
| 2005/0119754 A1 | 6/2005 | Trieu et al. |
| 2005/0169893 A1 | 8/2005 | Koblish et al. |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |
| 2006/0084602 A1 | 4/2006 | Lynch |
| 2006/0149392 A1 | 7/2006 | Hsieh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0233853 A1 | 10/2006 | Remington et al. |
| 2006/0247156 A1 | 11/2006 | Vanderby et al. |
| 2006/0292198 A1 | 12/2006 | Dalal et al. |
| 2007/0003752 A1 | 1/2007 | Bruce et al. |
| 2007/0026044 A1 | 2/2007 | Bunting et al. |
| 2007/0048381 A1 | 3/2007 | Hart et al. |
| 2007/0053951 A1 | 3/2007 | Gonzalez Santos et al. |
| 2007/0129807 A1 | 6/2007 | Lynch et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0207185 A1 | 9/2007 | Hart et al. |
| 2007/0218098 A1 | 9/2007 | Reif et al. |
| 2007/0244484 A1 | 10/2007 | Luginbuehl |
| 2007/0259018 A1 | 11/2007 | McKay |
| 2007/0259814 A1 | 11/2007 | Lynch |
| 2007/0260326 A1 | 11/2007 | Williams et al. |
| 2007/0282455 A1 | 12/2007 | Luginbuehl et al. |
| 2008/0027470 A1 | 1/2008 | Hart et al. |

| | | | |
|---|---|---|---|
| 2008/0193424 A1 | 8/2008 | McKale et al. | |
| 2008/0200372 A1 | 8/2008 | Ghosh | |
| 2009/0054339 A1 | 2/2009 | Marshall et al. | |
| 2009/0074753 A1 | 3/2009 | Lynch | |
| 2009/0092674 A1 | 4/2009 | Ingram et al. | |
| 2009/0130173 A1 | 5/2009 | Behnam et al. | |
| 2009/0232890 A1 | 9/2009 | Lynch et al. | |
| 2010/0136085 A1 | 6/2010 | Hart et al. | |
| 2010/0151025 A1 | 6/2010 | Lynch et al. | |
| 2010/0174368 A1 | 7/2010 | Lynch et al. | |
| 2010/0183515 A1 | 7/2010 | Hart et al. | |
| 2010/0196347 A1 | 8/2010 | Kery et al. | |
| 2010/0247651 A1 | 9/2010 | Kestler et al. | |
| 2011/0117018 A1 | 5/2011 | Hart et al. | |

FOREIGN PATENT DOCUMENTS

| | | |
|---|---|---|
| EP | 0 479 799 B1 | 4/1992 |
| EP | 0 530 804 A1 | 3/1993 |
| EP | 0 530 804 B1 | 3/1993 |
| EP | 00530804 A1 | 3/1993 |
| EP | 0741785 | 11/1996 |
| EP | 0 896 825 A1 | 2/1999 |
| EP | 0 896 825 B1 | 2/1999 |
| EP | 00741785 B2 | 11/1999 |
| EP | 0 994 694 B1 | 4/2000 |
| EP | 1 025 871 A1 | 8/2000 |
| EP | 01025871 A1 | 8/2000 |
| EP | 1 100 488 B1 | 5/2001 |
| EP | 1 146 897 B1 | 10/2001 |
| EP | 00896825 B1 | 7/2002 |
| EP | 1 234 552 A1 | 8/2002 |
| EP | 1 234 552 B1 | 8/2002 |
| EP | 01234552 B1 | 8/2002 |
| EP | 01146897 B1 | 9/2002 |
| EP | 1242129 | 9/2002 |
| EP | 01100488 B1 | 4/2003 |
| EP | 00994694 B1 | 10/2003 |
| EP | 1 374 857 A1 | 1/2004 |
| EP | 01374857 A1 | 1/2004 |
| EP | 1 410 811 A1 | 4/2004 |
| EP | 1 410 811 B1 | 4/2004 |
| EP | 01410811 A1 | 4/2004 |
| EP | 1 464 307 A1 | 10/2004 |
| EP | 1 464 307 B1 | 10/2004 |
| EP | 1 561 481 A2 | 8/2005 |
| EP | 1 561 481 A3 | 8/2005 |
| EP | 01561481 A2 | 8/2005 |
| EP | 1563846 | 8/2005 |
| EP | 01563846 A1 | 8/2005 |
| EP | 1 681 087 A2 | 7/2006 |
| EP | 01681067 A1 | 7/2006 |
| EP | A 681 087 A3 | 7/2006 |
| EP | 1 712 244 A1 | 10/2006 |
| EP | 1 719 531 A2 | 11/2006 |
| EP | 1 719 532 A2 | 11/2006 |
| EP | 01719531 A2 | 11/2006 |
| EP | 01719532 A2 | 11/2006 |
| GB | 2 367 497 A | 4/2002 |
| GB | 02367497 A | 4/2002 |
| JP | 7-250688 A | 10/1995 |
| JP | 2003-265592 A | 9/2003 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO 93/20859 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO 94/22463 | 10/1994 |
| WO | WO-94/22463 A1 | 10/1994 |
| WO | WO-94/26892 A1 | 11/1994 |
| WO | WO-94/26893 A1 | 11/1994 |
| WO | WO 94/28889 A1 | 12/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/16035 A3 | 6/1995 |
| WO | WO-95/18856 A1 | 7/1995 |
| WO | WO 95/20967 | 8/1995 |
| WO | WO-95/28124 A2 | 10/1995 |
| WO | WO-95/28124 A3 | 10/1995 |
| WO | WO 95/28950 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-96/17924 A3 | 6/1996 |
| WO | WO-97/13857 A1 | 4/1997 |
| WO | WO 98/00183 A2 | 1/1998 |
| WO | WO-98/00183 A2 | 1/1998 |
| WO | WO-98/00183 A3 | 1/1998 |
| WO | WO-98/40113 A1 | 9/1998 |
| WO | WO-98/41246 A2 | 9/1998 |
| WO | WO 98/41246 A2 | 9/1998 |
| WO | WO-98/41246 A3 | 9/1998 |
| WO | WO-98/51354 A2 | 11/1998 |
| WO | WO 98/51354 A2 | 11/1998 |
| WO | WO-98/51354 A3 | 11/1998 |
| WO | WO 99/30726 | 6/1999 |
| WO | WO-99/38543 A2 | 8/1999 |
| WO | WO-99/38543 A3 | 8/1999 |
| WO | WO 99/67289 | 12/1999 |
| WO | WO-00/04940 A1 | 2/2000 |
| WO | WO 01/32197 | 5/2001 |
| WO | WO 01/35932 | 5/2001 |
| WO | WO 01/41822 | 6/2001 |
| WO | WO 01/57083 A1 | 8/2001 |
| WO | WO-01/57083 A1 | 8/2001 |
| WO | WO 01/60424 | 8/2001 |
| WO | WO 01/66044 | 9/2001 |
| WO | WO 01/66044 A2 | 9/2001 |
| WO | WO 01/66130 | 9/2001 |
| WO | WO 01/68135 | 9/2001 |
| WO | WO-02/00244 A2 | 1/2002 |
| WO | WO-02/00244 A3 | 1/2002 |
| WO | WO-02/00272 A2 | 1/2002 |
| WO | WO 02/00272 A3 | 1/2002 |
| WO | WO-02/00272 A3 | 1/2002 |
| WO | WO 02/36147 A1 | 5/2002 |
| WO | WO-02/36147 A1 | 5/2002 |
| WO | WO 02/062405 | 8/2002 |
| WO | WO 02/067978 A1 | 9/2002 |
| WO | WO-02/067978 A1 | 9/2002 |
| WO | WO-02/070029 A2 | 9/2002 |
| WO | WO-02/070029 A3 | 9/2002 |
| WO | WO 02/102783 | 12/2002 |
| WO | WO 03/006025 | 1/2003 |
| WO | WO-03/043576 A2 | 5/2003 |
| WO | WO 03/043576 A2 | 5/2003 |
| WO | WO-03/043576 A3 | 5/2003 |
| WO | WO-03/065996 A2 | 8/2003 |
| WO | WO-03/065996 A3 | 8/2003 |
| WO | WO 03/070186 | 8/2003 |
| WO | WO-03/071997 A1 | 9/2003 |
| WO | WO 2004/002539 A2 | 1/2004 |
| WO | WO-2004/010907 A1 | 2/2004 |
| WO | WO 2004/010907 A1 | 2/2004 |
| WO | WO 2004/071543 A1 | 8/2004 |
| WO | WO-2004/073563 A2 | 9/2004 |
| WO | WO-2004-073563 A3 | 9/2004 |
| WO | WO 2005/046746 | 11/2004 |
| WO | WO-2004/110308 A2 | 12/2004 |
| WO | WO-2004/110308 A3 | 12/2004 |
| WO | WO-2004/110308 C2 | 12/2004 |

| | | |
|---|---|---|
| WO | WO 2005/009496 | 2/2005 |
| WO | WO 2005/032461 | 4/2005 |
| WO | WO-2005/042048 A2 | 5/2005 |
| WO | WO-2005/042048 A3 | 5/2005 |
| WO | WO-2005/046746 A1 | 5/2005 |
| WO | WO-2005/054279 A1 | 6/2005 |
| WO | WO-2005/054279 C1 | 6/2005 |
| WO | WO-2005/072656 A1 | 8/2005 |
| WO | WO-2006/031388 A2 | 3/2006 |
| WO | WO 2006/031388 A2 | 3/2006 |
| WO | WO-2006/031388 A3 | 3/2006 |
| WO | WO-2006/034365 A2 | 3/2006 |
| WO | WO-2006/034365 A3 | 3/2006 |
| WO | WO 2006/044334 A2 | 4/2006 |
| WO | WO-2006/050493 A2 | 5/2006 |
| WO | WO-2006/050493 A3 | 5/2006 |
| WO | WO-2006/093808 A1 | 9/2006 |
| WO | WO 2006/093808 A1 | 9/2006 |
| WO | WO-2006/133403 A2 | 12/2006 |
| WO | WO-2006/133403 A3 | 12/2006 |
| WO | WO-2007/061889 A2 | 5/2007 |
| WO | WO-2007/061889 A3 | 5/2007 |
| WO | WO-2007/087436 A2 | 8/2007 |
| WO | WO-2007/087436 A3 | 8/2007 |
| WO | WO-2007/089997 A2 | 8/2007 |
| WO | WO-2007/089997 A3 | 8/2007 |
| WO | WO-2007/090102 A2 | 8/2007 |
| WO | WO-2007/090102 A3 | 8/2007 |
| WO | WO-2007/092622 A2 | 8/2007 |
| WO | WO-2007/092622 A3 | 8/2007 |
| WO | WO-2008/005427 A2 | 1/2008 |
| WO | WO-2008/005427 A3 | 1/2008 |
| WO | WO-2008/073628 A2 | 6/2008 |
| WO | WO-2008/073628 A3 | 6/2008 |
| WO | WO-2008/103690 A2 | 8/2008 |
| WO | WO-2008/103690 A3 | 8/2008 |
| WO | WO-2008/151193 A1 | 12/2008 |
| WO | WO-2009/100454 A1 | 8/2009 |
| WO | WO-2010/030714 A2 | 3/2010 |
| WO | WO-2010/030714 A3 | 3/2010 |
| WO | WO-2010/071857 A1 | 6/2010 |
| WO | WO-2010/102266 A1 | 9/2010 |

OTHER PUBLICATIONS

Arm, D.M. et al., "Effect of Controlled Release of Platelet-derived Growth Factor from a Porous Hydroxyapatite Implant on Bone Ingrowth," *Biomaterials*, 1996, 17:703-709.

Cho, Moon II et al., "Platelet-derived Growth Factor—Modulated Guided Tissue Regenerative Therapy," Department of Oral Biology and Periodontal Disease Research Center School of Dental Medicine, State University of New York at Buffalo, Buffalo, NY, *J. Periodontal*, Jun. 1995, 66(6).

Hsu, M.D., Charles et al., "Clinical Implications of Growth Factors in Flexor Tendon Wound Healing," *The Journal of Hand Surgery*, Jul. 2004, 29(4).

Mitlak, B.H. et al., "The Effect of Systemically Administered PDGF-BB on the Rodent Skeleton," *Journal of Bone and Mineral Research*, 1996, 11(2).

Nakamura, N. et al., Early Biological Effect of In Vivo Gene Transfer of Platelet-derived Grown Factor (PDGF)-B into Healing Patellar Ligament, *Gene Therapy*, 1998, 5:1165-1170.

Nevins, M. et al., "Periodontal Regeneration in Humans Using Recombinant Human Platelet-derived Growth Factor-BB (rhPDGF-BB) and Allogenic Bone," *J. Periodontal*, Sep. 2003, 74(9).

Rasubala, L. et al., "Platelet-derived Growth Factor and Bone Morphogenetic Protein in the Healing of Mandibular Fractures in Rats," *British Journal of Oral and Maxillofacial Surgery*, 2003, 41:173-178.

Solheim, E., "Growth Factors in Bone," *International Orthopedics (SICOT)*, 1998, 22:410-416.

Spindler, K.P. et al., "Patellar Tendon and Anterior Curciate Ligament Have Different Mitogenic Responses to Platelet-derived Growth Factor and Transforming Growth Factor B," *Journal of Orthopedic Research*, 14:542-546, Jul. 1996.

Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7ware%...>, last visited on Feb. 24, 2010, 2 pages.

Adalberto et al. "Periodontal Regeneration," *J. Periodontal*, 2005, 76(9):1601-1622.

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7):971-977.

Advisory Action Before the Filing of an Appeal Brief mailed on Apr. 4, 2008, for U.S. Appl. No. 11/159,533, filed Jun. 23, 2005, 3 pages.

Advisory Action Before the Filing of an Appeal Brief mailed on Jun. 4, 2008, for U.S. Appl. No. 11/159,533, filed Jun. 23, 2005, 3 pages.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofacial Implants*; 2004, 19:59-65.

Ahn, S-H. et al. (Jun. 2003). "Effect of Recombinant Human Bone Morphogenetic Protein-4 with Carriers in Rat Calvarial Defects," *Journal of Periodontology* 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Masters Abstracts International* 46(6):61.

Amendment After Request for Continued Examination submitted on Aug. 7, 2008, for U.S. Appl. No. 11/159,533, filed Jun. 23, 2005, 18 pages.

Amendment and Response to Final Office Action submitted on Feb. 25, 2008, for U.S. Appl. No. 11/159,533, filed Jun. 23, 2005, 9 pages.

Amendment and Response to Non-Final Office Action submitted on Oct. 26, 2007, for U.S. Appl. No. 11/159,533, filed Jun. 23, 2005, 15 pages.

Amendment in Response to Non-Final Office Action submitted on Dec. 18, 2009, for U.S. Appl. No. 11/704,685, filed Feb. 9, 2007, 32 pages.

American Dental Association (Jun. 2006). Expert Panel Recommendations: Dental Management of Patients on Oral Bisphosphonate Therapy, *Report of the Council of Scientific Affairs*, 14 pages.

Anitua, E. et al. "Autologous platelets as a source of proteins for healing and tissue regeneration," *Thromb Haemost*, 2004, 91:4-15.

Anitua et al. (2005). "Autologous Preparations Rich in Growth Factors Promote Proliferation and Induce VEGF and HGF Production by Human Tendon Cells in Culture," *Journal of Orthopaedic Research* 23:281-286.

Anonymous (2003). "The European Market for Dental Bone Graft Substitutes," *Implant Dentistry* 12(1):3-5.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," in *Cancer Cells 3: Growth Factors and Transformations*, Fermasico, J. et al. eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, *J. Dental Res*. 70:536.

Anusaksathien et al. "Growth Factor Delivery to Re-Engineer Periodontal Tissues," *Current Pharmaceutical Biotechnology*, 2002, vol. 3(2):129-139.

Anusaksathien et al. "Platelet-Derived Growth Factor Gene Delivery Stimulates ex Vivo Gingival Repair," *Tissue Engineering*, 2003, 9(4):745-758.

Anusaksathien et al. "Effect of Sustained Gene Delivery of Platelet-Derived Growth Factor or Its Antagonist (PDGF-1308) on Tissue-Engineered Cementum," *J. Periodontal*, Mar. 2004, 75(3):429-440.

Assael, L.A. (2006). "A Time for Perspective on Bisphosphonates," *J. Oral Maxillofac. Surg*. 64:877-879.

Babbush, C.A. DDS MSCD et al. "An In Vitro and In Vivo Evaluation of Autologous Platelet Concentrate in Oral Reconstruction," *Implant Dent*., 2003, 12(1):24-34.

Barker, K. et al. (Jun. 2006). "Bisphosphonate-Associated Osteonecrosis of the Jaws: A Guide for the General Dental Practitioner," *Dental Update* pp. 270-275.

Basa, S. et al. (2004). "Alternative Bone Expansion Technique for Immediate Placement of Implants in the Edentulous Posterior Mandibular Ridge: A Clinical Report," *International Journal of Oral & Maxofacial Implants* 19(4):554-558.

Bateman, J. et al. "Platelet-Derived Growth Factor Enhancement of Two Alloplastic Bone Matrices," *J. Periodontol.* (Nov. 2005) 76(11):1833-1841.

Becker. W. et al. (Nov. 1992). "A Comparison of PTFE Membranes Alone or in Combination with Platelet-Derived Growth Factor and Insulin-Like Growth Factor-I, or Demineralized Freeze Dried Bone in Promoting Bone Formation Around Immediate Extraction Socket Implants: A Study in Dogs," *J. Periodtonol.* 63(11):929-940.

Berlemann, U. et al. (2002). "Adjacent Vertebral Failure After Vertebroplasty," *J. Bone Joint Surg.* Br 84(B):748-752.

Betsholtz, C. et al. (Apr. 24, 1986). "cDNA Sequence and Chromosomal Localization of Human Platelet-Derived Growth Factor A-Chain and its Expression in Tumour Cell Lines," *Nature* 320:695-699.

Biomimetic Therapeutics (Aug. 21, 2002). "Orthovita and BioMimetic Enter into a Supply Agreement," located at <http://biomimetics.com/cgi-bin/aw/acuweb.cgi?s=biomimetics&t=pressreleasedtl.htm&StoryID=82&>, last visited on May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressreleasedtl.htm&StoryID=76&>, last visited on May 18, 2010, 5 pages.

Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressreleasedtl.htm&StoryID=83&>, last visited on May 18, 2010, 6 pages.

Biomimetic Therapeutics (Jul. 15, 2004). "BioMimetic Pharmaceuticals' Receives Approvable Recommendation from FDA Advisory Panel for *GEM 21S®*," located at <http://biomimetics.com/cgi-bin/aw/acuweb.cgi?s=biomimetics&t=pressreleasedtl.htm&StoryID=78&>, last visited on May 18, 2010, 6 pages.

Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressreleasedtl.htm&StoryID=79&>, last visited on May 20, 2010, 5 pages.

Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressreleasedtl.htm&StoryID=80&>, last visited on May 18, 2010, 6 pages.

Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressreleasedtl.htm&StoryID=81&>, last visited on May 20, 2010, 6 pages.

Biomimetic Therapeutics (Nov. 21, 2005). "BioMimetic Therapeutics Announces FDA Approval of *GEM 21S®* Growth-Factor Enhanced Matrix for the Treatment of Periodontally-Related Bone Defects," located at <http://biomimetics.com/cgi-bin/aw/acuweb.cgi?s=biomimetics&t=pressreleasedtl.htm&StoryID=87&>, last visited on May 18, 2010, 6 pages.

Biomimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics&t=pressreleasedtl.htm&StoryID=118&>, last visited on May 18, 2010, 6 pages.

Biomimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&t=NewsDetail.htm&StoryID=166&>, 5 pages.

Biomimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.

Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at <http://biomimetics.com/cgi-bin/aw/acuweb.cgi?s=biomimetics&t=pressreleasedtl.htm&StoryID=94&>, last visited on May 18, 2010, 6 pages.

Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressreleasedtl.htm&StoryID=97&>, last visited on May 20, 2010, 6 pages.

Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID=101&>, last visited on May 18, 2010, 7 pages.

Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedtl.htm&StoryID=104&>, last visited on May 18, 2010, 7 pages.

Biomimetic Therapeutics (Jan. 25, 2007). "BioMimetic Therapeutics Reports Positive Clinical Results Using *GEM OS® 1* to Treat Distal Radius Fractures," located at <http://biomimetics.com/cgi-bin/aw/acuweb.cgi?s=biomimetics&t=pressreleasedtl.htm&StoryID=105&>, last visited on May 18, 2010, 6 pages.

Biomimetic Therapeutics (Feb. 21, 2007). "BioMimetic Therapeutics Receives Orphan Drug Designation for rhPDGF-BB Treatment of Osteonecrosis of the Jaw," located at <http://biomimetics.com/cgi-bin/aw/acuweb.cgi?s=biomimetics&t=pressreleasedtl.htm&StoryID=112&>, last visited on Apr. 5, 2010, 6 pages.

Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at <http://biomimetics.com/cgi-bin/aw/acuweb.cgi?s=biomimetics&t=pressreleasedtl.htm&StoryID=113&>, last visited on May 18, 2010, 8 pages.

Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressreleasedtl.htm&StoryID=111&>, last visited on May 18, 2010, 4 pages.

Biomimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressreleasedtl.htm&StoryID=116&>, last visited on May 18, 2010, 7 pages.

Biomimetic Therapeutics (Jun. 7, 2007). "BioMimetic Therapeutics Initiates Enrollment in E.U. Registration Trial for GEM OS®1 Bone Graft; U.S. GEM OS1 Pivotal Study Protocol Amended to Allow Shorter Follow-Up Time and More Patients," located at <http://biomimetics.com/cgi-bin/aw/acuweb.cgi?s=biomimetics&t=pressreleasedtl.htm&StoryID=119&>, last visited on May 18, 2010, 6 pages.

Biomimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics&t=pressreleasedtl.htm&StoryID=123&>, last visited on May 18, 2010, 8 pages.

Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressreleasedtl.htm&StoryID=125&>, last visited on May 18, 2010, 7 pages.

Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressreleasedtl.htm&StoryID=127&>, last visited on May 18, 2010, 7 pages.
Biomimetic Therapeutics (Dec. 13, 2007). "BioMimetic Therapeutics reports Positive Clinical Results for GEM OS®1 in Canadian Foot and Ankle Fusion Study; Clinical Success Rate of 90% Achieved in High Risk Patient Population," located at <http://biomimetics.com/cgi-bin/aw/acuweb.cgi?s=biomimetics&t=pressreleasedtl.htm&StoryID=131&>, last visited on May 18, 2010, 6 pages.
Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm&StoryID=149&>, last visited on May 18, 2010, 7 pages.
Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressreleasedtl.htm&StoryID=136&>, last visited on May 18, 2010, 6 pages.
Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.
Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137&>, last visited on May 18, 2010, 8 pages.
Biomimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/acuweb.cgi?s=biomimetics&t=pressreleasedtl.htm&StoryID=151&>, last visited on May 18, 2010, 8 pages.
Biomimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics&t=pressreleasedtl.htm&StoryID=153&>, last visited on May 18, 2010, 7 pages.
Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.
Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressreleasedtl.htm&StoryID=157&>, last visited on May 18, 2010, 8 pages.
Biomimetic Therapeutics (Nov. 21, 2008). "BioMimetic Therapeutics, Inc. Announces Patent Allowance from the United States Patent and Trademark Office for PDGF Compositions Patent; Expanded Protection for Augment™, Augment™ Injectable and GEM 21S® Until 2024," located at <http://biomimetics.com/cgi-bin/aw/acuweb.cgi?s=biomimetics&t=pressreleasedtl.htm&StoryID=163&>, last visited on May 18, 2010, 5 pages.
Biomimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics&t=pressreleasedtl.htm&StoryID=169&>, last visited on May 18, 2010, 5 pages.

Biomimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl.htm&StoryID=168&>, last visited on May 18, 2010, 5 pages.
Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at <http://biomimetics.com/cgi-bin/aw/acuweb.cgi?s=biomimetics&t=pressreleasedtl.htm&StoryID=154&>, last visited on May 18, 2010, 6 pages.
Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressreleasedtl.htm&StoryID=160&>, last visited on May 18, 2010, 11 pages.
Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressreleasedtl.htm&StoryID=167&>, last visited on May 18, 2010, 8 pages.
Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressreleasedtl.htm&StoryID=185&>, last visited on May 18, 2010, 8 pages.
Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at <http://biomimetics.com/cgi-bin/aw/acuweb.cgi?s=biomimetics&t=pressreleasedtl.htm&StoryID=188&>, last visited on May 18, 2010, 8 pages.
Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressreleasedtl.htm&StoryID=190&>, last visited on May 18, 2010, 6 pages.
Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/cgi-bin/aw/acuweb.cgi?s=biomimetics&t=pressreleasedtl.htm&StoryID=191&>, last visited on May 18, 2010, 8 pages.
Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressreleasedtl.htm&StoryID=199&>, last visited on May 18, 2010, 5 pages.
Biomimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at <http://biomimetics.com/cgi-bin/aw/acuweb.cgi?s=biomimetics&t=pressreleasedtl.htm&StoryID=201&>, last visited on May 18, 2010, 6 pages.
Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressreleasedtl.htm&StoryID=202&>, last visited on May 18, 2010, 6 pages.
Biomimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics&t=pressreleasedtl.htm&StoryID=203&>, last visited on May 18, 2010, 11 pages.
Biomimetic Therapeutics (Mar. 12, 2010). "Morningstar® Document Research$^{SM}$ Form 10-K," United States Securities and Exchange Commission Annual Report, located at <http://investor.biomimetics.com/phoenix.zhtml?c=196896&p=irol-sec>, last visited on May 19, 2010, 247 pages.

Björkenheim, J.M. (1989). "Structure and Function of the Rabbit's Supraspinatus Muscle After Resection of its Tendon," *Acta Orthop. Scand.* 60(4):461-463.

Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.

Bolander, "Regulation of Fracture Repair by Growth Factors," *P.S. E.B.M.*, 1992, 200:165-170.

Bonfini, T. et al. (Jan. 1, 2006). "Autologous Marrow and Platel Gel in Bone Tissue Regeneration," *Cytotherapy* 8(1), Abstract No. 239, 2 pages.

Bora, F.W. Jr. et al. (Aug. 1987). "Joint Physiology, Cartilage Metabolism, and the Etiology of Osteoarthritis," *Hand Clin.* 3(3):325-336.

Boyden, E.M. et al. (Aug. 1995). "Late Versus Early Repair of Achilles Tendon Rupture: Clinical and Biomechanical Evaluation," *Clin. Orthop. Relat. Res.* 317:150-158.

Braddock, M. et al. (Oct. 2001). "Born Again Bone: Tissue Engineering for Bone Repair," *News Physiool. Sci.* 16:208-213.

Buser, D. et al. (1991). "Effects of Growth Factors on Bone Regeneration Around Titanium Implants," Abstract No. 282, *J. Dental Res.* 70:301.

Business Wire. (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at <http://www.highbeam.com/doc/1G1-68027113.html>, last visited on Apr. 26, 2010, 3 pages.

Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3 pages.

Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.

Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.

Camelo et al. "Clinical, radiographic, and histologic evaluation of human periodontal defects treated with bio-oss and bio-guide," *International Journal of Periodontics and Restorative Dentistry*, 1998, 18(4):321-332.

Camelo et al. "Periodontal regeneration with an autogenous bone-bio-oss composite graft and a bio-guide membrane," *International Journal of Periodontics and Restorative Dentistry*. 2001, 21(2):109-120.

Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," *International Journal of Periodontics & Restorative Dentistry* 23(3):213-225.

Canalis, "Effect of Growth Factors on Bone Cell Replication and Differentiation," *Clinical Orthopedics and Related Research*, Mar. 1985, 193:246-263.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol.* 71(1):1743-1749.

Catalano, L. et al. (2006). "Bisphoshonates and Risk of Osteonecorisis of the Jaws," *Haema* 9(3):410-414.

Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand.* 74(5):559-564.

Cenni, E. et al. (2005, e-pub. Feb. 1, 2005). "Plasma Levels of Platelet-Derived Growth Factor BB and Transforming Growth Factor in Patients with Failed Hip Protheses," *Acta Orthopaedica* 76(1):64-66.

Chen et al. "Adenoviral Gene Transfer of PDGF Downregulates *Gas* Gene Product PDGFR and Prolongs ERK and AktIPKB Activation," *Am J Physiol Cell Physiol.*, Mar. 2002, 282:C538-C544.

Chiandussi, S. et al. (2006). "Clinical and Diagnostic Imaging of Bisphosphonate-Associated Osteonecrosis of the Jaws," *Dentomaxillofacial Radiology* 35:236-243.

Chin, M. (1995). "Distraction Osteogenesis in Maxillofacial Surgery," Chapter 9 in *Tissue Engineering: Applications in Maxillofacial Surgery and Periodontics*, Lynch, S.E. et al. eds., Quintessence Publishing, pp. 147-159.

Clergeau, C.P. et al. (Feb. 1996). "Healing Response to Anorganic Bone Implantation in Periodontal Intrabony Defects in Dogs Part 1. Bone Regeneration. A Microradiographic Study," *J. Periodontool.* 67(2):140-149.

Cochran et al. "Effects of Platelet-Derived Growth Factor Isoforms on Calcium Release From Neonatal Mouse Calvariae," *Bone*, 1993, 14:53-58.

Coleman, S.H. et al. (Dec. 2003). "Chronic Rotator Cuff Injury and Repair Model in Sheep," *The Journal of Bone and Joint Surgery* 85-A(12):2391-2402.

Collins, T. et al. (Aug. 22, 1985). "Cultured Human Endothelial Cells Express Platelet-Derived Growth Factor B Chain: cDNA Cloning and Structural Analysis," *Nature* 316:748-750.

Convery, F.R. et al. (Jan.-Feb. 1972). "The Repair of Large Osteochondral Defects. An Experimental Study in Horses," *Clin. Orthop. Relat. Res.* 82:253-262.

Cooke et al. "Effect of rhPDGR-BB Delivery on Mediators of Periodontal Wound Repair," *Tissue Engineering*, 2006, 12(6):1441-1450.

Cossolin, G.S.I. et al. ( Date Unknown) "Treatment of Avascular Osteonecrosis of the Jaws in Cancer Patients with a Histroy of Bisphosphonate Therapy by Combining Bone Resection and Autologous Platelet-Rich Plasma," *Hospital Santa Catarina* 10 pages.

Costa, M.A. et al. (Jul. 2006). "Tissue Engineering of Flexor Tendons: Optimization of Tenocyte Proliferation Using Growth Factor Supplementation," *Tissue Eng.* 12(7):1937-1943.

Courneya, J-P. et al. (2010). "Normal and Diseased Primary Human Tenocytes in Response to rhPDGF-BB," Poster No. 1118, *56th Annual Meeting of the Orhopaedic Research Society*, located at <http://www.ors.org/web/Transactions/56/1118.pdf>, last visited on Feb. 23, 2010, 1 page.

Curi et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," *Journal of Oral and Maxillofacial Surgery* 65(2):349-355.

Dalla-Favera, R. et al. (Nov. 12, 1982). "Chromosomal Localization of the Human Homolog (*c-sis*) of the Simian Sarcoma Virus *onc* Gene," *Science* 218:686-688.

Daniels, T.R. et al. (2008). "Application of rhPDGF-BB in Foot and Ankle Fusion Procedures," Chapter 19 in *Tissue Engineering: Applications in Maxillofacial Surgery and Periodontics*, Second Edition, Lynch, S.E. et al. eds., Quintessence Publishing Co.: Hanover Park, IL, pp. 267-275.

Doolittle et al. (Jul. 15, 1983). "Simian Sarcoma Virus *onc* Gene *v-sis*, Is Derived from the Gene (or Genes) Encoding a Platelet-Derived Growth Factor," *Science* 221 :275-277.

Duffy, F.J. et al. (Jul. 1995). "Growth Factors and Canine Flexor Tendon Healing: Initial Studies in Uninjured and Repair Models," *The Journal of Hand Surgery* 20A(4):645-649.

Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.

Easley, M.E. et al. (May 2000). "Isolated Subtalar Arthodesis," *JBJS* 82-A(5):613-624.

Eastell, R. et al. (Mar. 1991). "Classification of Vertebral Fractures," *J. Bone Miner. Res.* 6(3):207-215.

Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent.* 28(1):37-43.

Farrugia, M.C. et al. (Jan. 2006). "Osteonecrosis of the Mandible or Maxilla Associated with the Use of New Generation Bisphosphonates," *The Laryngoscope* 116:115-120.

Feldman, D. et al. (Sep. 1998). "In a Time of Change, Orthopedics Sector is Marked by New Modalities," *The BBI Newsletter*, located at <http://findarticles.com/p/articles/mi_m3570/is_n9_v21/ai_n27541529>, last visited on Mar. 12, 2009, 2 pages.

Fennis et al. "Mandibular reconstruction: A clinical and radiographic animal study on the use of autogenous scaffolds and platelet-rich plasma," *Int. J. Oral Maxillofac. Surg.*, 2002, 31:281-286.

Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.

Ficarra, G. et al. (2005). "Osteonecrosis of the Jaws in Periodontal Patients with a History of Bisphophonates Treatment," *J. Clin. Periodontol.* 32:1123-1128.

Final Office Action mailed on Feb. 7, 2008, for U.S. Appl. No. 11/159,533, filed Jun. 23, 2005, 8 pages.

Finkelman, R.D. et al. (1995). "Systematic PDGF ± Alendronate Increases Bone Density in OVX Rats," Abstract No. 1281, *J. Dental Res.* 74:172.

Fontana et al. "Effect of Platelet-Rich Plasma on the Peri-implant Bone Response: An Experimental Study," *Implant Dentistry*, 2004, 13:73-78.

Freedonia (Sep. 2006). "Biocompatible Materials. US Industry Study with Forecasts to 2010 & 2015," Study #2111, located at <http://www.freedoniagroup.com/pdf/2111smwe.pdf>, last visited on Jun. 17, 2010, 8 pages (Table of Contents Only.).

Fribourg, D. et al. (Oct. 15, 2004). "Incidence of Subsequent Vertebral Fracture After Kyphoplasty," *Spine* 29(20):2270-2276.

Fukui, A. et al. (Sep. 1993). "Isolation and Characterization of *Xenopus* Follistatin and Activins," *Devel. Biol.* 159(1):131-139.

Galatz, L.M. et al. (Feb. 2004). "The Outcome and Repair Integrity of Completely Arthoscopically Repaired Large and Massive Rotator Cuff Tears," *J. Bone Joint Surg. Am.* 86-A(2):219-244.

Gamradt, S.C. et al. (Mar. 2007). "Platelet Rich Plasma in Rotator Cuff Repair," *Tech. In Orthop.* 22(1):26-33.

Garg, A.K. (1995). "Grafting Materials in Repair and Restoration," Chapter 5 in *Tissue Engineering: Applications in Maxillofacial Surgery and Periodontics*, Lynch, S.E. et al. eds., Quintessence Publishing, pp. 83-101.

Garg, "The Use of Platelet-Rich Plasma to Enhance the Success of Bone Grafts Around Dental Implants," *Dental Implantology Update*, Mar. 2000, 11(3):17-21.

Gazielly, D.F. et al. (Jul. 1994). "Functional and Anatomical Results After Rotator Cuff Repair," *Clin. Orthop. Relat. Res.* 304:43-53.

Gerber, C. et al. (May 1994). "Mechanical Strength of Repairs of the Rotator Cuff," *J. Bone Joint Surg. Br.* 76-B(3):371-380.

Gerber, C. et al. (Apr. 2000). "The Results of Repair of Massive Tears of the Rotator Cuff," *J. Bone Joint Surg. Am.* 82-A(4):505-515.

Giannobile, W.V. et al. (1994). "Synergistic Effects of Insulin-Like Growth Factors -I (IGF-I) with Other Growth Factors on Bone Formation in vitro," Abstract No. 831, *J. Dental Res.* 73:205.

Giannobile et al. "Comparison of Canine and Non-Human Primate Animal Models for Periodontal Regenerative Therapy: Results Following a Single Administration of PDGF/IGF-I," *J. Periodontol*, Dec. 1994, 65(12):1158-1168.

Giannobile, W.V. et al. (Nov. 1995). "Platelet Derived Growth Factor (PDGF) and Insulin-Like Growth Factor (IGF-I) Enhances Periodontal Regeneration in *Macaca fascicularis*," Abstract No. 28, *Advanced Dental Research* 9(3 Suppl.):29.

Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.

Giannobile et al. "Periodontal Tissue Engineering by Growth Factors," *Bone*, Jul. 1996, 19(1), Supplement: 23S-37S.

Giannobile et al. "Non-Coordinate Control of Bone Formation Displayed by Growth Factor Combinations with IGF-I," *J Dent Res*, Sep. 1997, 76(9):1569-1578.

Giannobile et al. "Recombinant Human Osteogenic Protein-1 (OP-1) Stimulates Periodontal Wound Healing in Class III Furcation Defects," *J Periodontol*, Feb. 1998, 69(2):129-137.

Giannobile, "Platelet-Derived Growth Factor (PDGF) Gene Delivery for Application in Periodontal Tissue Engineering," *J Periodontol*, Jun. 2001, 72(6):815-823.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Gilbertson et al. "Platelet-derived Growth Factor C (PDGF-C), a Novel Growth Factor That Binds to PDGF $\alpha$ and $\beta$ Receptor," *The Journal of Biological Chemistry*, Jul. 20, 2001, 276(29):27406-27414.

Goutalier, D. et al. (Jul. 1994). "Fatty Muscle Degeneration in Cuff Ruptures: Pre- and Postoperative Evaluation by CT Scan," *Clin. Orthop.* 304:78-83.

Grageda, "Platelet-Rich Plasma and Bone Graft Materials: A Review and a Standardized Research Protocol," *Implant Dentistry*, 2004, 13(4):301-309.

Green et al. "Immunolocalization of platelet-derived growth factor A and B chains and PDGF-$\alpha$ and $\beta$-receptors in human gingival wounds," *Journal of Periodontal Research*, 1997, 32(2):209-214.

Gronwald et al. "Cloning and expression of a cDNA coding for the human platelet-derived growth factor receptor: Evidence for more than one receptor class," *Proc. Natl. Acad. Sci. USA*, May 1988, 85:3435-3439.

Hanel, D.P. et al. (Jan. 2002). "Wrist Fractures," *Orthop. Clin. North Am.* 33(1):35-57.

Harryman, D.T. et al. (Aug. 1991). "Repairs of the Rotator Cuff," *J. Bone Joint Surg. Am.* 73-A(7):982-989.

Hart, C.E. et al. "Purification of PDGF-AB and PDGF-BB from Human Platelet Extracts and Identification of All Three PDGF Dimers in Human Platelets," *Biochemistry*, Jan. 9, 1990, 29(1):166-172.

Hart et al. "Synthesis, Phosphorylation, and Degredation of Multiple Forms of the Platelet-derived Growth Factor Receptor Studied Using a Monoclonal Antibody," *The Journal of Biological Chemistry*, Aug. 5, 1987, 262(22):10780-10785.

Hart et al. "Two Classes of PDGF Receptor Recognize Different Isoforms of PDGF," *Science*, Jun. 1988, 240:1529-1531.

Hattrup, S.J. et al. (1985). "A Review of Ruptures of the Achilles Tendon," *Foot & Ankle* 6(1):34-38.

Hee et al. (2003). "Do Autologous Growth Factors Enhance Transformational Lumbar Interbody Fusion?" *Eur. Spine. J.* 12(4):400-407.

Heini, P.F. et al. (2001, e-pub. Jun. 14, 2001). "Bone Substitutes in Vertebroplasty," *Eur. Spine J.* 10:S205-S213.

Helm et al. (Apr. 2001). "Bone Graft Substitutes for the Promotion of Spinal Arthrodesis," *Neurosur. Foc.* 10(4):1-5.

Higashi, T. et al. (Jun. 1996). "Influence of Particle Size of Calcium Phosphate Ceramics as a Capping Agent on the Formation of a Hard Tissue Barrier in Amputated Dental Pulp," *Journal of Endodontics* 22(6):281-283.

Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.

Hollinger, J.O. et al. (Feb. 2008). "Recombinant Human Platelet Derived Growth Factor: Biology and Clinical Applications," *J. Bone & Joint Surgery* 90-A(Suppl. 1):48-54.

Hollinger, J.O. et al. (2008). "Therapeutic Opportunities for Bone Grafting," Chapter 68 in *Principles of Regenerative Medicine*, Atala, A. et al. eds., Academic Press: Burlington, MA, pp. 1164-1175.

Hollinger, J.O. et al. (2008). "Protein Therapeutics and Bone Healing," Chapter 1 in *Tissue Engineering: Applications in Maxillofacial Surgery and Periodontics*, Second Edition, Lynch, S,E. et al. eds., Quintessence Publishing Co.: Hanover Park, IL, pp. 3-25.

Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate-Craniofacial Journal* 33(4):277-283.

Howell, T.H. et al. (1996). "Polypeptide Growth Factors for Periodontal Regeneration," *Current Opinion in Periodontology* 3:149-156.

Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J Periodontol.*, Dec. 1997, 68(12):1186-1193.

Howes et al. "Platelet-Derived Growth Factor Enhances Demineralized Bone Matrix-Induced Cartilage and Bone Formation," *Calcif Tissue Int.*, 1988, 42:34-38.

Ikezawa et al. "Characterization of Cementum Derived Growth Factor as an Insulin-Like Growth Factor-I Like Molecule," *Connective Tissue Research*, 1997, 36(4):309-319.

International Search Report mailed on Aug. 3, 2007, for PCT Application No. PCT/US2007/003582, filed on Feb. 9, 2007, 2 pages.

International Search Report mailed on Oct. 2, 2007, for PCT Application No. PCT/US05/36447, filed on Oct. 12, 2005, 1 page.

Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.

Jensen et al. "Platelet rich plasma and fresh frozen bone allograft as enhancement of implant fixation—An experimental study in dogs," *Journal of Orthopaedic Research*, 2004, 22:653-658.

Jensen, O.T. et al. (2008). "Alveolar Distraction Osteogenesis and Tissue Engineering," Chapter 14 in *Tissue Engineering: Applications in Maxillofacial Surgery and Periodontics*, Second Edition, Lynch, S.E. et al. eds., Quintessence Publishing Co.: Hanover Park, IL, pp. 203-219.

Jensen, O.T. (2008). "Dentoalveolar Modification with an Osteoperiosteal Flap and rhPDGF-BB," Chapter 15 in *Tissue Engineering: Applications in Maxillofacial Surgery and Periodontics*, Second Edition, Lynch, S.E. et al. eds., Quintessence Publishing Co.: Hanover Park, IL, pp. 220-225.

Jiang, D. et al. "Modification of an Osteoconductive Anorganic Bovine Bone Miami Matrix with Growth Factors," *J. Periodonlol.*, Aug. 1999, 70(8):834-839.

Jin et al. "Engineering of Tooth-Supporting Structures by Delivery of PDGF Gene Therapy Vectors," *Molecular Therapy*, Apr. 2004, 9(4):519-526.

Jin, Q. et al. (Mar. 5, 2008). "Nanofibrous Scaffolds Incorporating PDGF-BB Microspheres Induce Chemokine Expression and Tissue Neogenesis In Vivo," *PLoS ONE* 3(3):e1729, pp. 1-9.

Jones et al. (1992). "Isolation of Vgr-2, a Novel Member of the Transforming Growth Factor—Beta-related Gene Family," *Mol Endocnnol.* 6(11):1961-1968.

Jozsa, L. et al. (Aug. 1989). "Fibronectin and Laminin in Achilles Tendon," *Acta Orthop Sacninavica* 60(4):469-471.

Kademani, D. et al. (Aug. 2006). "Primary Surgical Therapy for Osteonecrosis of the Jaw Secondary to Bisphosphonate Therapy," *Mayo Clin. Proc.* 81(8):1100-1103.

Kaigler, "Growth factor delivery for oral and periodontal tissue engineering," *Expert Opin Drug Deliv.*, 2006, 3(5):647-662.

Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.

Kassolis et al. "Alveolar Ridge and Sinus Augmentation Utilizing Platelet-Rich Plasma in Combination with Freeze-Dried Bone Allograft: Case Series," *Journal of Periodontology*, Oct. 2000, 71(10):1654-1661.

Kazlauskas et al. "Different effects of homo- and heterodimers of platelet-derived growth factor A and 8 chains on human and mouse fibroblasts," *The EMBO Journal* (1988) 7 (12):3727-3735.

Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.

Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.

Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.

Kovacs et al. "Comparative Study of $\beta\beta$-Tricalclum Phosphate Mixed with Platelet-Rich Plasma versus $\beta$-Tricalcium Phosphate, A Bone Substitute Material in Dentistry," *Acts Veterinaria Hungarica*, 2003, 51(4):475-484.

Kovacevic, D. et al. (Mar. 2008). "Biological Augmentation of Rotator Cuff Tendon Repair," *Clin. Orthop. Relat. Res.* 466(3):622-633.

Landesberg et al. "Quantification of Growth Factor Levels Using a Simplified Method of Platelet-Rich Plasma Gel Preparation," *J. Oral Maxillofac. Surg.*, 2000, 58:297-301.

Lasa et al. "Delivery of Demineralized Bone Powder by Fibrin Sealant," *Plast. Reconstr. Surg.*, 1995, 96(6):1409-1417.

Lasa Jr., C. et al. (1996). "Bone Induction by Demineralized Bone Powder and Partially Purified Osteogenin Using a Fibrin-Sealant Carrier," Chapter 14 in *Surgical Adhesives and Sealants: Current Technology and Applications*, Sierra, D. et al. eds., Technomic Publishing Company, Inc.: Lancaster, PA, pp. 135-144.

Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.

Lee, S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.

Lee et al. "Enhanced bone formation by controlled growth factor delivery from chitosan-based biomaterials," *Journal of Controlled Release*, 2002, 78:187-197.

Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.

Letson, A.K. et al. (1994). "The Effect of Combinations of Growth Factors on Ligament Healing," *Clinical Orhopaedics and Related Research* 308:207-212.

Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO., Sep. 9-13, 1994, p. S135.

Liang et al. (Sep. 2000). "Effect of Cytokines on Repair of Tendon Injury," *Pub Med* 14(5):283-285, Abstract Only.

Lind et al. (1998). "Growth Factor Stimulation of Bone Healing," *Acta Orthopaedica Scandinavica Supplementum* Suppl. 283:2-37.

Lioubavina-Hack et al. "Methyl cellulose gel obstructed bone formation by GBR: an experimental study in rats," *J. Clin. Periodontol.*, 2005, 32:1247-1253.

Lipshitz, H. et al. (Jun. 1975). "In Vitro Wear of Cartilage," *J. Bone Joint Surg. Am.* 57A(4):527-534.

Lynch, S.E. et al. (Nov. 1987). "Role of Platelet-Derived Growth Factor in Wound Healing: Synergistic Effects with Other Growth Factors," *Proc. Natl. Acad. Sci. USA* 84:7696-7700.

Lynch, S.E. et al. (1988). "Synergistic Effects of Recombinant Platelet-Derived Growth Factor Two and Insulin-Like Growth Factor-I in Wound Healing," Abstract No. 585, *J. Dental Res.* 67:186.

Lynch, S.E. et al. (1988). "Potential Role of Platelet-Derived and Insulin-Like Growth Factors in Periodontal Regeneration," Abstract No. 586, *J. Dental Res.* 67:186.

Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. et al. (1989). "Comparative Effects of Growth Factors on Soft Tissue Repair," Abstract No. 1153, *J. Dental Res.* 68:326.

Lynch, S.E. (1990). "A Possible Role for Polypeptide Growth and Differentiation Factors in Periodontal Regeneration," *Executive Committee on Chemotherpeutics; Amer. Acad Peridontal—Position Paper* pp. 1-4.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7):458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontol.* 62(11):710-717.

Lynch, S.E. (1991). "Platelet-Derived Growth Factor and Insulin-Like Growth Factor. I: Mediators of Healing Soft Tissue and Bone Wounds," *Periodontol Case Reports Ne Soc. Periodontists Bull.* 13(2):13-20.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration Abstract*, 2(1):84.

Lynch, S.E. et al. (1994). "Polypeptide Growth Factors: Molecular Mediators of Tissue Repair," Chapter 33 in *Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 in *Periodontal Regeneration: Current Status and Directions*, Polson, A. ed., Quintessence Publishing Co, Inc: Chicago, IL, 11:179-197.

Lynch, S.E. (1995). "Introduction," in *Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 in *Bone Regeneration and Repair: Biology and Clinical Applications*, Lieberman, J.R. et al. eds., Humana Press Inc.: Totowa, NJ, pp. 359-390.

Lynch, S.E. et al. (Dec. 2006). "A New Era in Periodontal and Periimplant Regeneration: *Use of Growth-Factor Enhanced Matrices Incorporating rhPDGF,*" *Compendium of Continuing Education in Dentistry* 27(12):672-679.

Lynch, S.E. et al. (2008). "Use of rhPDGF to Improve Bone and Periodontal Regeneration," Chapter 6 in *Tissue Engineering: Applications in Maxillofacial Surgery and Periodontics*, Second Edition, Lynch, S.E. et al. eds., Quintessence Publishing Co.: Hanover Park, IL, pp. 87-102.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Manske et al. (Feb. 1985). "Flexor Tendon Healing," *Symposium on Flexor Tendon Surgery, Hand Clinics* 1(1):25-34.

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Marx, R.E. (2008). "Application of Tissue Engineering Principles to Clinical Practice," Chapter 4 in *Tissue Engineering: Applications in Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 in *Tissue Engineering: Applications in Maxillofacial Surgery and Periodontics*, Second Edition, Lynch, S.E. et al. eds., Quintessence Publishing Co.: Hanover Park, IL, pp. 132-144.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister, B. et al. (1998). "Long-term Evaluation of Sinus Grafting with Bio-Oss® in the Chimpanzee," Abstract No. 1097, *J. Dental Res.* 77:769.

McAllister et al. "Eighteen-month Radiographic and Histologic Evaluation of Sinus Grafting with A-rganic Bovine Bone in the Chimpanzee," *The International Journal of Oral & Maxillofacial Implants*, 1999, 14(3):361-368.

McGuire, M.K. et al. (2006). "rhPDGF-BB Promotes Healing of Periodontal Defects: 24-Month Clinical and Radiographic Observations," *Int. J. Periodontics Restorative Dent.* 26(3):223-231.

McGuire, M.K. (2008). "Soft Tissue Engineering Applications in Dentistry," Chapter 7 in *Tissue Engineering: Applications in Maxillofacial Surgery and Periodontics*, Second Edition, Lynch, S.E. et al. eds., Quintessence Publishing Co.: Hanover Park, IL, pp. 103-118.

McMurty, R.Y. et al. (1992). "Fractures of the Distal Radius," Chapter 35 in *Skeletal Trauma*, Browner B.D. et al. eds., W.B. Saunders Company: Philadelphia, PA, 2:1063-1094.

Mehta, V. et al. (Apr.-Jun. 2005). "The Use of Growth Factors on Tendon Injuries," *Journal of Hand Therapy* 18:87-92.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:16751681.

Migliorati, C.A. et al. (Jun. 2006). "Bisphosphate-Associated Osteonecrosis: A Long Term Complication of Bisphosphonate Treatment," *Lancet Oncol.* 7:508-514.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in In Vitro Wound Model," *J. Periodontal.* 72(3):331-340.

Nakamura, N. et al. (1998). "Early Biological Effect of In Vivo Gene Transfer of Platelet-derived Grown Factor (PDGF)-B into Healing Patellar Ligament," *Gene Therapy* 5:1185-1170.

Nancollas, G.H. et al. (2006, e-pub. Jul. 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Rest. Dent.* 23(1):9-17.

Nevins, M.L. et al. (2005). "Three-Dimensional Micro-Computed Tomographic Evaluation of Periodontal Regeneration: A Human Report of Intrabony Defects Treated with Bio-Oss Collagen," *Int. J. Periodontics Restorative Dent.* 25(4):365-373.

Nevins et al. "Platelet-Derived Growth Factor Stimulates Bone Fill and Rate of Attachment Level Gain: Results of a Large Multicenter Randomized Controlled Trial," *J. Periodontal*, 2005, 76(12):2205-2215.

Nevins, M. et al. (Oct. 2007). "Clinical Results Using Recombinant Human Platelet-Derived Growth Factor and Mineralized Freeze-Dried Bone Allograft in Periodontal Defects," *Int. J. Periodontics Restorative Dent.* 27(5):421-427.

Nevins, M. et al. (2008). "Treatment of Advanced Periodontal Defects Using Bioactive Therapies," Chapter 5 in *Tissue Engineering: Applications in Maxillofacial Surgery and Periodontics*, Second Edition, Lynch, S.E. et al. eds., Quintessence Publishing Co.: Hanover Park, IL, pp. 67-86.

Nevins, M.L. et al. (2008). "Site Development for Implant Placement: Regenerative and Esthetic Techniques in Oral Plastic Surgery," Chapter 8 in *Tissue Engineering: Applications in Maxillofacial Surgery and Periodontics*, Second Edition, Lynch, S.E. et al. eds., Quintessence Publishing Co.: Hanover Park, IL, pp. 119-131.

Nickols, J.C. et al. (2008). "The Role of Growth Factors in Tendon Healing," Chapter 20 in *Tissue Engineering: Applications in Maxillofacial Surgery and Periodontics*, Second Edition, Lynch, S.E. et al. eds., Quintessence Publishing Co.: Hanover Park, IL, pp. 276-289.

Nociti, F.H. Jr. et al. (2000). "Histometric Evaluation of Bone Regeneration Around Immediate Implants Partially in Contact with Bone: A Pilot Study in Dogs," *Implant Dentistry* 9(4):321-328.

Non-Final Office Action mailed on Jul. 27, 2007, for U.S. Appl. No. 11/159,533, filed Jun. 23, 2005, 13 pages.

Non-Final Office Action mailed on Oct. 31, 2008, for U.S. Appl. No. 11/159,533, filed Jun. 23, 2005, 11 pages.

Non-Final Office Action mailed on Oct. 16, 2009, for U.S. Appl. No. 11/704,685, filed Feb. 9, 2007, 19 pages.

Notice of Allowance mailed on Apr. 23, 2010, for U.S. Appl. No. 11/704,685, filed Feb. 9, 2007, 10 pages.

Oberg, S. et al. (Apr. 1994). "Bone Healing After Implantation of Hydroxyapatite Granules and Bblocks (Interpore 200) Combined with Autolyzed Antigen-Extracted Allogeneic Bone and Fibrin Glue. Experimental Studies on Adult Rabbits," *International Journal of Oral and Maxillofacial Surgery* 23(2):110-114, abstract only.

Orbay, J.L. et al. (Jan. 2004). "Volar Fixed-Angle Plate Fixation for Unstable Distal Radius Fractures in the Elderly Patient," *J. Hand Surg.* 29A(1):96-102.

Orthovita, Inc. (Dec. 14, 2000). "510(k) Summary. *Vitoss™ Scaffold* Syntehtic Cancellous Bone Void Filler," located at <http://www.accessdata.fda.gov/cdrh_docs/pdf/k994337.pdf>, last visited on Mar. 30, 2010, 6 pages.

Orthovita, Inc. (Nov. 19, 2002). "Morningstar® Document Research™. Form 10-Q, Quarterly Repot Which Provides a Continuing View of a Company's Financial Position," located at <http://orthovita.com/investors/secfilings.aspx>, last visited on Jun. 17, 2010, 48 pages.

Orthovita, Inc. (2009). "Architects of the New Biomaterials Age, 2008 Annual Report," located at <http://orthovita.com/investors/annual-reports/previousreports.aspx>, last visited on Jun. 17, 2010, 93 pages.

Owen et al. (1984). "Simian Sarcoma Virus-Transformed Cells Secrete a Mitogen Identical to Platelet-Derived Growth factor," *Science* 25:54-56.

Palti, A. et al. (2002). "A Concept for the Treatment of Various Dental Bone Defects," *Implant Dentistry* 11(1):73-78.

Parashis, A. et al. (Jul. 1998). "Comparison of 2 Regenerative Procedures—Guided Tissue Regeneration and Demineralized Freeze-Dried Bone Allograft—in the Treatment of Intrabony Defects: A Clinical and Radiographic Study," *J. Periodontal.* 69(7):751-758.

Park et al. (1995). "Periodontal Regeneration in Class III Furcation Defects of Beagle Dogs Using Guided Tissue Regenerative Therapy with Platelet-Derived Growth Factor," *J. Periodontol.* 66:462-477.

Paul, W. et al. (1999). "Development of Porous Spherical Hydroxyapatite Granules: Application Towards Protein Delivery," *J. Mater. Sci. Mater. Med.* 10:383-388.

Persson, G.R. et al. (2000). "A Retrospective Radiographic Outcome Assessment Study of Intra-Bony Defects Treated by Osseous Surgery or by Bone Graft Procedures," *J. Clin. Periodontol.* 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts,"*Arch. Orthop. Trauma Surg.* 123(9):485-488.

Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor," *Endocrinology* 127(1):69-75.

Philippart et al. "Human Recombinant Tissue Factor, Platelet-rich Plasma, and Tetracycline Induce a High-Quality Human Bone Graft A 5-year Survey," *The International Journal of Oral and Maxillofacial Implants*, 2003, 18(3):411-416.

Phillips, S. et al. (1988). "The Direct Medical Costs of Osteoporosis for American Woman Aged 45 and Older, 1986," *Bone* 9(4):271-279.

Pickett, F.A. (Jul. 2006). "Bisphosphonate-Associated Osteonecrosis of the Jaw: A Literature Review and Clinical Practice Guidelines," *Journal of Dental Hygiene* 80(3):1-12.

Polverini, P.J. (Aug. 2002). "Angiogenesis in Health and Disease: Insights into Basic Mechanisms and Therapeutic Opportunities," *Journal of Dental Education* 66(8):962-975.

R&D Systems, Inc. (Date Unknown). "Quantikine® Human PDGF-BB Immunoassay," *Package Insert*, Catalog No. DBB00, SBB, and PDB00, located at <http://www.rndsystems.com/pdf/dbb00.pdf>, last visited on Mar. 30, 2010, 16 pages.

Rao, C.D. et al. (Apr. 1986). "Structure and Sequence of the Human c-*sis*/Platelet-Derived Growth Factor 2 (*SIS/PDGF2*) Transcriptional Unit," *Proc. Natl. Acad. Sci. USA* 83:2392-2396.

Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," *Int. J. Mol. Med.* 23(3):407-413, Abstract Only, 2 pages.

Response to Advisory Action submitted on Apr. 28, 2008, for U.S. Appl. No. 11/159,533, filed Jun. 23, 2005, 15 pages.

Response to Notice of Non-Compliant Amendment submitted on Nov. 2, 2007, for U.S. Appl. No. 11/159,533, filed Jun. 23, 2005, 7 pages.

Robbins, K.C. et al. (Oct. 13, 1983). "Structural and Immunological Similarities Between Simian Sarcoma Virus Gene Product(s) and Human Platelet-Derived Growth Factor," *Nature* 305:605-608.

Rodeo, S.A. et al. (Dec. 1993). "Tendon Healing in a Bone Tunnel," *J. Bone Joint Surg. Am.* 75-A(12):1795-1803.

Rodeo, S.A. et al. (1999). "Use of Recombinant Human Bone Morphogenic Protein-2 to Enhance Tendon Healing in a Bone Tunnel," *Am. J. Sports Med.* 27(4):476-488.

Rodriguez et al. "Maxillary Sinus Augmentation with Deproteinated Bovine Bone and Platelet Rich Plasma with Simultaneous Insertion of Endosseous Implants," *J. Oral Maxiilofac. Surg.*, 2003, 61 :157-163.

Rohrich et al. (Nov. 1999). "Mersilene Suture as a Vehicle for Delivery of Growth Factors in Tendon Repair," *Journal of the American Society of Plastic Surgeons* 104(6):1713-1717.

Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/journal/10792104>, 8 pages.

Ruiz, G. et al. (1991). "Short Term Administration of Growth Factors Enhances Periodontal Regeneration," Abstract No. 1615, *J. Dental Res.* 70:468.

Russell, T.A. et al. (Date Unknown). "Trigen® IM Nail System Surgical Technique. Trochanteric Antegrade Nail (TAN™)," 24 pages.

Rutherford et al. (1992). "Platelet-Derived and Insulin-Like Growth Factors Stimulate Regeneration of Periodontal Attachment in Monkeys," *Journal of Periodontal Research* 27(4-Part 1):285-290.

Sandberg, "Matrix in Cartilage and Bone Development: Current Views on the Function and Regulation of Major Organic Components," *Annals of Medicine*, 1991, 23:207-217.

Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res.* 14(3):369-372.

Sasai, Y. et al. (Dec. 2, 1994). "Xenopus *chordin*: A Novel Dorsalizing Factor Activated by Organizer-Specific Homeobox Genes," *Cell* 79:779-790.

Saygin et al. "Molecular and Cell Biology of Cementum," *Periodontology*, 2000, 24:73-98.

Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.

Schmidt et al. "A review of the effects of insulin-like growth factor and platelet derived growth factor on in vivo cartilage healing and repair," *Osteoarthritis and Cartilage*, 2006, 14(5):403-412.

Schmidt, M.B. et al. (2008). "Tissue Engineering Strategies in the Treatment of TMDs," Chapter 18 in *Tissue Engineering: Applica-* tions in *Maxillofacial Surgery and Periodontics*, Second Edition, Lynch, S.E. et al. eds., Quintessence Publishing Co.: Hanover Park, IL, pp. 252-264.

Schmitt, J.M. et al. (Nov. 1997). "Comparison of Porous Bone Mineral and Biologically Active Glass in Critical-Sized Defects," *J. Periodontol.* 68(11):1043-1053.

Secinfo.Com (Mar. 31, 2003). "Interpore International Inc/DE 10-K for Dec. 31, 2002," located at <http://www.secinfo.com/dV179.2kp.htm, last visited on May 20, 2010, 57 pages.

Shahgaldi, B.F. et al. (Jan. 1991). "Repair of Cartilage Lesions Using Biological Implants. A Comparative Histological and Biomechanical Study in Goats," *J. Bone Joint Surg. Br*. 73-B(1):57-64.

SIGMA (Date Unknown). "Platelet Derived Growth Factor-BB," Product Information Sheet, 2 pages.

Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.

Simion, M. et al. (1994). "Vertical Ridge Augmentation Using a Membrane Technique Associated with Osseointegrated Implants," *Int. J. Periodontics Restorative Dent.* 14(6):497-511.

Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.

Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.

Simion, M. et al. (1999). "Effect of Different Microstructures of e-PTFE Membranes on Bone Regeneration and Soft Tissue Response: A Histologic Study in Canine Mandible," *Clin. Oral Implants Res*. 10:73-84.

Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.

Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.

Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81 (8):1013-1022.

Smith & Nephew (Date Unknown). "Trigen. Humeral Nail," Surgical Technique Pamphlet, 27 pages.

Spector, M. (2008). "Basic Principles of Scaffolds in Tissue Engineering," Chapter 2 in *Tissue Engineering: Applications in Maxillofacial Surgery and Periodontics*, Second Edition, Lynch, S.E. et al. eds., Quintessence Publishing Co.: Hanover Park, IL, pp. 26-36.

Spindler, K.P. et al. (1995). "Proliferative Response to Platelet-Derived Growth Factor in Young and Old Rat Patellar Tendon," *Connective Tissue Research* 31(2):171-177.

Spindler, K.P. et al. (Jul. 1996). "Patellar Tendon and Anterior Cruciate Ligament Have Different Mitogenic Responses to Platelet-Derived Growth Factor and Transforming Growth Factor β," *Journal of Orthopaedic Research* 14(4):542-546.

Stephan, E.B. et al. (Apr. 1999). "Anogranic Bovine Bone Supports Osteoblastic Cell Attachment and Proliferation," *J. Periodontol.* 70(4):364-369.

Stephan et al. "Platelet-Derived Growth Factor Enhancement of a Mineral-Collagen Bone Substitute," *J. Periodontal*, Dec. 2000, 71:1887-1892.

Strom, T.B. (Sep. 6, 2005). "Saving Islets from Allograft Rejection," *PNAS USA* 102(36):12651-12652.

Suba et al. "Facilitation of β-Tricalcium Phosphate-Induced Alveolar Bone Regeneration by Platelet-Rich Plasma in Beage Dogs: A Histologic and Histomorphometric Study," *The International J. of Oral and Maxillofacial Implants*, 2004, 19(6):832-838.

Supplemental Response to Advisory Action of Jun. 4, 2008, submitted on Jun. 9, 2008, for U.S. Appl. No. 11/159,533, filed Jun. 23, 2005, 15 pages.

Supplementary European Search Report mailed on Aug. 29, 2008, for EP Application No. 05803356.4, filed on Oct. 12, 2005, 7 pages.

Tadic, D. et al. (2004). "A Novel Method to Produce Hydroxyapatite Objects with Interconnecting Porosity that Avoids Sintering," *Biomaterials* 25(16):3335-3340.

Tamai, N. et al. (2002). "Novel Hydroxyapatite Ceramics with an Interconnective Porous Structure Exhibit Superior Osteoconduction in vivo," *J. Biomed. Mater. Res.* 59:110-117.

Teraoka, K. et al. (2004). "Construction of an Interconnected Pore Network Using Hydroxyapatite Beads," *Key. Eng. Mater*. 254-256:257-259.

Teraoka, K. et al. (Sep. 2004). "Construction of Interconnected Pore Network Using Hydroxyapatite Small Components," *Trans. Mater. Res. Soc. Jpn.* 29(6):2919-2921.

Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.

Tinti, C. et al. (1996). "Vertical Ridge Augmentation: What is the Limit?" *Int. J. Periodontics Restorative Dent*. 16(3):221-229.

TRENDING123.Com (Date Unknown). "Stock Sectors. Medical Instruments Supls," located at <http://www.trending123.com/stock-sectors/Medical_Instruments_Supls.html>, last visited on May 3, 2010, 11 pages.

U.S. Appl. No. 10/965,319, filed Oct. 14, 2004, by Lynch.

U.S. Appl. No. 12/556,555, filed Sep. 9, 2009, by Lynch et al.

Van Den Wyngaert, T. et al. (Aug. 2006). "Bisphosphonates and Osteonecrosis of the Jaw: Cause and Effect or a *post hoc* Fallacy?" *Annals of Oncology* 17(8):1197-1204.

Venkatasatya, M. et al. (2008). The Effect of PDGF, Vitamin D and PTH on Osteoblasts Derived From Patients on Chronic Bisphosphonate Therapy, Dissertation for The State University of New York at Buffalo, located at <http://gradworks.umi.com/14/531/1453440.html>, last visited on Mar. 31, 2010, 2 pages, Abstract Only.

Virchenko, O. et al. (2008, e-pub. Jul. 4, 2008). "Early Achilles Tendon Healing in Sheep," *Arch. Orthop. Trauma Surg.* 128:1001-1006.

Visnapuu et al. "Distribution of fibroblast growth factors (FGFR-1 and -3) and platelet-derived growth factor receptors (PDGFR) in the rat mandibular condyle during growth," *Orthod. Craniofadal.* 2002, 5:147-153.

Walter, C. et al. (2006, e-pub. Aug. 29, 2006). "Prevalence of Bisphophonate Associated Osteonecrosis of the Jaw within the Filed of Osteonecrosis," *Support Care Center* 6 pages.

Wang, Y. et al. (Feb. 23, 1996). "A Large Family of Putative Transmembrane Receptors Homologous to the Product of the Drosophila Tissue Polarity Gene *Frizzled*," *J. Biol. Chem.* 271(8):4468-4476.

Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.

Wang, X.T. et al. (Sep. 2004). "Tendon Healing in Vitro: Genetic Modification of Tenocytes With Exogenous PDGF Gene and Promotion of Collagen Gene Expression," *The Journal of Hand Surgery* 29A(5):884-890.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.

Wei et al. "Nano-Fibrous Scaffold for Controlled Delivery of Recombinant Human PDGF-BB," *Journal of Controlled Release*, 2006, e-pub. Mar. 3, 2006, 112:103-110.

Wiesen, R.J. et al. (1998). "Efficacy of Bovine Bone Mineral in Vertical Osseous Defects," Abstract No. 1165, *J. Dental Res*. 77:777.

Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.

Wikesjö et al. (1989). "Effects of Subgingival Irrigation on A. actinomycetemcomitans," *J. Clin. Perrodont.* 16:116-119.

Williams et al. "Tissue Engineering: What Does It Mean? Why Is It Important?" *Compendium*, Jan. 2005, 26(1):54-60.

Wisner-Lynch, L.A. (Oct. 2006). "From Passive to Active: Will Recombinant Growth Factor Therapeutics Revolutionize Regeneration?" *Int. J. Periodont. And Rest. Dent*. 26(5):409-411.

Woo, S.L-Y. et al. (1998). "Engineering the Healing of the Rabbit Medical Collateral Ligament," *Medical and Biological Engineering and Computing* 36:359-364.

Woo, S-B. et al. (May 16, 2006). "Systematic Review: Bisphosphonates and Osteonecrosis of the Jaws," *Annals of Internal Medicine* 144(10):753-761.

Written Opinion of the International Searching Authority mailed on Aug. 3, 2007, for PCT Application No. PCT/US07/003582, filed on Feb. 8, 2007, 7 pages.

Written Opinion of the International Searching Authority mailed on Oct. 2, 2007, for PCT Application No. PCT/US05/36447, filed on Oct. 12, 2005, 4 pages.

Written Opinion of the International Searching Authority mailed on Dec. 7, 2007, for PCT Application No. PCT/US2006/044766 filed on Nov. 17, 2006, 6 pages.

Yang, C. et al. (2003). "Vascular Endothelial Growth Factor Gene Transfection to Enhance the Repair of Avascular Necrosis of the Femoral Head of Rabbit," *Chinese Medical Journal* 116(10):1 544-1548.

Yazawa et al. "Basic Studies on the Clinical Applications of Platelet-Rich Plasma," *Cell Transplantation*, 2003, 12:509-518.

Yazawa, M. et al. (May 2004). "Basic Studies on the Bone Formation Ability by Platelet Rich Plasma in Rabbits," *Journal of Craniofacial Surgery* 15(3):439-446.

Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-110.

Younger, E.M. et al. (1989). "Morbidity at Bone Graft Donor Sites," *J. Orthop. Trauma* 3(3):192-195.

Zavras, A.I. et al. (2006). "Bisphosphonates Are Associated With Increased Risk for Jaw Surgery in Medical Claims Data: Is it Osteonecrosis?" *J. Oral Maxillofac. Surg*. 64:917-923.

Zhu et al. "Gene Transfer and Expression of Platelet-Derived Growth Factors Modulate Periodontal Cellular Activity," *J. Dent Res*, 2001, 80(3):892-897.

Zimmer, Inc. (2005). "Zimmer® Collagen Repair Patch," Product No. 04-4100-001-00, 6 pages.

Adalberto et al., "Periodontal Regeneration," J. Periodontal, 2005, 76(9): 1601-1622.

Aghaloo, T.L. DDS MD et al., "Evaluation of Platelet-Rich Plasma in Combination with A-rganic Bovine Bone in the Rabbit Cranium: A Pilot Study," The International Journal of Oral and Maxillofacial Implants, 2004, 19:59-65.

Anitua, E. et al., "Autologous platelets as a source of proteins for healing and tissue regeneration," Thromb Haemost, 2004, 91:4-15.

Anusaksathien et al., "Effect of Sustained Gene Delivery of Platelet-Derived Growth Factor or Its Antagonist (PDGF—1308) on Tissue-Engineered Cementum," J. Periodontal, 2004, 75(3): 429-440.

Anusaksathien et al., "Growth Factor Delivery to Re-Engineer Periodontal Tissues," Current Pharmaceutical Biotechnology, 2002, vol. 3(2): 129-139.

Anusaksathien et al., "Platelet-Derived Growth Factor Gene Delivery Stimulates ex Vivo Gingival Repair," Tissue Engineering, 2003, 9(4): 745-756.

Arm, et al. Effect of Controlled Release of Platelet-derived Growth Factor from a Porous Hydroxyapatite Implant on Bone Ingrowth, Biomaterials 17 (1996) 703-709.

Babbush, C.A. DDS MSCD et al., "An In Vitro and In Vivo Evaluation of Autologous Platelet Concentrate in Oral Reconstruction," Implant Dent., 2003, 12:24-34.

Bateman, et al. Platelet-Derived Growth Factor Enhancement of Two Alloplastic Bone Matrices, J. Periodontol. (2005) 76: 1833-1841.

BMP Gene Delivery for Alveolar Bone Engineering at Dental Implant Defects—Molecular Therapy, vol. 11, -. Feb. 2, 2005.

Bolander, "Regulation of Fracture Repair by Growth Factors," *P.S. E.B.M.*, 1992, 200: 165-170.

Camargo, et al, "Platelet-rich plasma and bovine porous bone mineral combined with guided tissue regeneration in the treatment of intrabony defects in humans," J Periodont Res 2002, 37: 300-306.

Camargo, L.V. PM et al., "Effectiveness of a combination of platelet-rich plasma, bovine porous bone mineral and guided tissue regeneration in the treatment of mandibular grade II molar furcations in humans," J. Clin. Periodontol, 2003, 30:746-751.

Camelo et al., "Clinical, radiographic, and histologic evaluation of human periodontal defects treated with bio-oss and bio-guide," International Journal of Periodontics and Restorative Dentistry, 1998, 18(4): 321-332.

Camelo et al., "Periodontal regeneration with an autoge-us bone-bio-oss composite graft and a bio-guide membrane," International Journal of Periodontics and Restorative Dentistry. 2001, 21(2): 109-120.

Canalis, "Effect of Growth Factors on Bone Cell Replication and Differentiation," *Clinical Orthopedics and Related Research*, 1985, 193: 246-263.

Chen et al., "Ade-viral Gene Transfer of PDGF Downregulates Gas Gene Product PDGFR and Prolongs ERK and Akt/PKB Activation," Am J Physiol Cell Physiol 282: C538-C544, 2002.

Cho et al., "Platelet-derived Growth Factor—Modulated Guided Tissue Regenerative Therapy," J Periodontal, 1995, 66(6): 522-530.

Cochran, et al. "Effects of Platelet-Derived Growth Factor Isoforms on Calcium Release From Neonatal Mouse Calvariae," Bone, 1993, 14: 53-58.

Cooke et al., "Effect of rhPDGR-BB Delivery on Mediators of Periodontal Wound Repair," Tissue Engineering, 2006, 12(6): 1441-1450.

Fennis, et al, "Mandibular reconstruction: A clinical and radiographic animal study on the use of autoge-us scaffolds and platelet-rich plasma," Int. J. Oral Maxillofac. Surg., 2001, 31: 281-286.

Fennis, et al, "Mandibular reconstruction: a histological and histomorphometric study on the use of autoge-us scaffolds, particulate cortico-cancellous bone grafts and platelet rich plasma in goats," Int. J. Oral Maxillofac. Surg., 2004, 33: 48-55.

Fontana, et al, "Effect of Platelet-Rich Plasma on the Peri-implant Bone Response: An Experimental Study," Implant Dentistry, 2004, 13: 73-78.

Garg, "The Use of Platelet-Rich Plasma to Enhance the Success of Bone Grafts Around Dental Implants," Dental lmplantology Update, 2000, 11(3): 41-44.

Giannobile et al., "Comparison of Canine and -n-Human Primate Animal Models for Periodontal Regenerative Therapy: Results Following a Single Administration of PDGF/IGF-I.," J. Periodontol 1994, 65: 1158-1168.

Giannobile et al., "-n-Coordinate Control of Bone Formation Displayed by Growth Factor Combinations with IGF-I," J Dent Res, 1997, 76(9): 1569-1578.

Giannobile et al., "Periodontal Tissue Engineering by Growth Factors," Bone, 1996, 19, Supplement: 23S-37S.

Giannobile et al., "Recombinant Human Osteogenic Protein-1 (OP-1) Stimulates Periodontal Wound Healing in Class III Furcation Defects," J Periodontol, 1998, 69:129-137.

Giannobile, "Platelet-Derived Growth Factor (PDGF) Gene Delivery for Application in Periodontal Tissue Engineering," J Periodontol, 2001, 72: 815-823.

Gilbertson et al., "Platelet-derived Growth Factor C (PDGF-C), a -vel Growth Factor That Binds to PDGF a and b Receptor," The Journal of Biological Chemistry, 2001, 276(29): 27406-27414.

Grageda, "Platelet-Rich Plasma and Bone Graft Materials: A Review and a Standardized Research Protocol," Implant Dentistry, 2004, 13(4): 301-309.

Green et al., "Immunolocalization of platelet-derived growth factor A and B chains and PDGF- and receptors in human gingival wounds," Journal of Periodontal Research, 1997, 32(2): 209-214.

Gronwald et al., "Cloning and expression of a cDNA coding for the human platelet-derived growth factor receptor: Evidence for more than one receptor class," Proc. Natl. Acad. Sci. USA, 1988, 85: 3435-3439.

Hart et al., "Purification of PDGF-AB and PDGF-BB from Human Platelet Extracts and Identification of All Three PDGF Dimers in Human Platelets," Biochemistry, 1990, 29: 166-172.

Hart et al., "Synthesis, Phosphorylation, and Degredation of Multiple Forms of the Platelet-derived Growth Factor Receptor Studied Using a Mo-clonal Antibody," The Journal of Biological Chemistry, 1987, 262(22): 10780-10785.

Hart et al., "Two Classes of PDGF Receptor Recognize Different Isoforms of PDGF," Science, 1988, 240: 1529-1531.

Howell et al.. "A Phase I/II Clinical Trial to Evaluate a Combination of Recombinant Human Platelet-Derived Growth Factor-BB and Recombinant Human Insulin-Like Growth Factor-I in Patients with Period. Dis.," J. Periodontol., 1997, 68(12): 1186-1193.

Howes et al., "Platelet-Derived Growth Factor Enhances Demineralized Bone Matrix-Induced Cartilage and Bone Formation," *Calcif Tissue Int.*, 1988, 42: 34-38.

Hsu, MD. et al., "Clinical Implications of Growth Factors in Flexor Tendon Wound Healing," The Journal of Hand Surgery, 2004, 29(4): 551-563.

Ikezawa et al., "Characterization of Cementum Derived Growth Factor as an Insulin-Like Growth Factor-I Like Molecule," Connective Tissue Research, 1997, 36(4): 309-319.

Jensen et al, "Platelet rich plasma and fresh frozen bone allograft as enhancement of implant fixation—An experimental study in dogs," Journal of Orthopaedic Research, 2004, 22: 653-658.

Jiang et al., "Modification of an Osteoconductive A-rganic Bovine Bone Mieral Matrix with Growth Factors," J. Periodontol., 1999, 70(8): 834-839.

Jin et al., "Engineering of Tooth-Supporting Structures by Delivery of PDGF Gene Therapy Vectors," Molecular Therapy, 2004, 9: 519-526.

Kaigler, "Growth factor delivery for oral and periodontal tissue engineering," Expert Opin Drug Deliv., 2006, 3(5): 1742-5247.

Kassolis et al., "Alveolar Ridge and Sinus Augmentation Utilizing Platelet-Rich Plasma in Combination with Freeze-Dried Bone Allograft: Case Series," Journal of Periodontology, 2000, 71(10):1654-1661.

Kazlauskas, et al. Different effects of homo- and heterodimers of platelet-derived growth factor A and B chains on human and mouse fibroblasts, The EMBO Journal (1988) 7 (12): 3727-3735.

Kim et al, "A Comparative Study of Osseointegration of Avana Implants in a Demineralized Freeze-Dried Bone Alone or With Platelet-Rich Plasma," J Oral Maxillofac Surg, 2002, 60:1018-1025.

Kim et al, "Use of Particulate Dentin-Plaster of Paris Combination with/without Platelet-Rich Plasma in the Treatment of Bone Defects Around Implants," The International Journal of Oral & Maxillofacial Implants, 2002; 17:86-94.

Kovacs et al, "Comparative Study of b-Tricalcium Phosphate Mixed with Platelet-Rich Plasma versus b-Tricalcium Phosphate, A Bone Substitute Material in Dentistry," Acta Veterinaria Hungarica, 2003, 51(4):475-484.

Landesberg et al, "Quantification of Growth Factor Levels Using a Simplified Method of Platelet-Rich Plasma Gel Preparation," J. Oral Maxillofac Surg, 2000, 58: 297-300.

Lasa et al, "Chapter 14: Bone Induction by Demineralized Bone Powder and Partially Purified Osteogenin Using a Fibrin-Sealant Carrier," Surgical Adhesives and Sealants: Current Technology and Applications. Ed.DH Sierra and R Saltz. Lancaster, PA:Technomics publishing AG, 1996. 135-143.

Lasa et al, "Delivery of Demineralized Bone Powder by Fibrin Sealant," Plast. Reconstr. Surg., 1995, 96: 1409.

Lee et al., "The bone regenerative effect of platelet-derived growth factor-BB delivered with a chitosan/tricalcium phosphate sponge carrier," *J. Periodontol.*, 2000, 71(3): 418-424.

Lee et al., "Enhanced bone formation by controlled growth factor delivery from chitosan-based biomaterials," *Journal of Controlled Release*, 2002, 78: 187-197.

Lekovic, et al, "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," J Periodontol, 2002; 73: 198-205.

Lioubavina-Hack et al., "Effect of Bio-Oss with or without platelet-derived growth factor on bone formation by 'guided tissue regeneration': a pilot study in rats," J Clin. Periodontol, 2003, 32: 1254-1260.

Lioubavina-Hack et al., "Methyl cellulose gel obstructed bone formation by GBR: an experimental study in rats," J. Clin. Periodontol., 2005, 32: 1247-1253.

Maiorana et al, "Maxillary Sinus Augmentation with A-rganic Bovine Bone (Bio-Oss) and Autologous Platelet-Rich Plasma: Preliminary Clinical and Histologic Evaluations," Int J Periodontics Restorative Den, 2003, 23: 227-235.

McAllister et al., "Eighteen-month Radiographic and Histologic Evaluation of Sinus Grafting with A-rganic Bovine Bone in the Chimpanzee," The International Journal of Oral & Maxillofacial Implants, 1999, 14(3): 361-368.

Mitlak et al., "The Effect of Systemically Administered PDGF-BB on the Rodent Skeleton," Journal of Bone and Mineral Research, 1996, 11(2): 238-247.

Nevia et al., "The Effect of Platelet-Rich Plasma on the Coronally Advanced Flap Root Coverage Procedure: A Pilot Human Trial," J. Periodontal, 2005, 76(10): 1768-1777.

Nevins et al., "Periodontal Regeneration in Humans Using Recombinant Human Platelet-derived Growth Factor-BB (rhPDGF-BB) and Allogenic Bone," J. Periodontal, 2003, 74(9): 1282-1292.

Nevins et al., "Platelet-Derived Growth Factor Stimulates Bone Fill and Rate of Attachment Level Gain: Results of a Large Multicenter Randomized Controlled Trial," J. Periodontal, 2005, 76(12): 2205-2215.

Philippart et al., "Human Recombinant Tissue Factor, Platelet-rich Plasma, and Tetracycline Induce a High-Quality Human Bone Graft: A 5-year Survey," The International Journal of Oral and Maxillofacial Implants, 2003, 118: 411-416.

Rasubala et al., "Platelet-derived Growth Factor and Bone Morphogenetic Protein in the Healing of Mandibular Fractures in Rats," British Journal of Oral and Maxillofacial Surgery, 2003, 41: 173-178.

Rodriguez et al., "Maxillary Sinus Augmentation with Deproteinated Bovine Bone and Platelet Rich Plasma with Simultaneous Insertion of Endosseous Implants," J. Oral Maxillofac. Surg., 2003, 61:157-163.

Sandberg, "Matrix in Cartilage and Bone Development: Current Views on the Function and Regulation of Major Organic Components," *Annals of Medicine*, 1991, 23: 207-217.

Sarment et al., "Effect of rhPDGF-BB on Bone Turnover During Periodontal Repair," J. Clin Periodontol, 2006, 33: 135-140.

Saygin et al., "Molecular and Cell Biology of Cementum," Periodontology, 2000, 24: 73-98.

Schmitt et al., "A review of the effects of insulin-like growth factor and platelet derived growth factor on in vivo cartilage healing and repair," Osteoarthritis and Cartilage, 2006, 14(5): 403-412.

Solheim, "Growth Factors in Bone," International Orthopaedics (SICOT), 1998, 22: 410-416.

Stephan et al., "Platelet-Derived Growth Factor Enhancement of a Mineral-Collagen Bone Substitute," J. Periodontol, 2000, 71: 1887-1892.

Suba et al., "Facilitation of b-Tricalcium Phosphate-Induced Alveolar Bone Regeneration by Platelet-Rich Plasma in Beagle Dogs: A Histologic and Histomorphometric Study," The International J. of Oral and Maxillofacial Implants, 2004, 19(6):832-838.

Visnapuu et al., "Distribution of fibroblast growth factors (FGFR-1 and -3) and platelet-derived growth factor receptors (PDGFR) in the rat mandibular condyle during growth," *Orthod. Craniofacial*, 2002, 5: 147-153.

Wei et al., "Na—Fibrous Scaffold for Controlled Delivery of Recombinant Human PDGF-BB," Journal of Controlled Release, 2006, 112: 103-110.

Williams et al., "Tissue Engineering: What Does It Mean? Why Is It Important?" Compendium, 2005, 26(1): 54-60.

Yazawa et al, "Basic Studies on the Clinical Applications of Platelet-Rich Plasma," Cell Transplantation, 2003, 12: 509-518.

Zhu et al., "Gene Transfer and Expression of Platelet-Derived Growth Factors Modulate Periodontal Cellular Activity," J. Dent Res, 2001, 80(3):892-897.

Extended European Search Report mailed on Jul. 26, 2010, for EP Patent Application No. 10166327.3, filed on Oct. 10, 2005, 6 pages.

Non-Final Office Action mailed on Jul. 7, 2010, for U.S. Appl. No. 12/323,183, filed Nov. 25, 2008, 11 pages.

White, E. et al. (Jan. 1986). "Biomaterial Aspects of Interpore-200 Porous Hydroxyapatite," *Dent. Clin. North Am.* 30(1):49-67, Abstract Only.

Amendment in Response to Non-Final Office Action submitted on Oct. 6, 2010, for U.S. Appl. No. 12/323,183, filed Nov. 25, 2008, 11 pages.

Final Office Action mailed on Jan. 7, 2001, for U.S. Appl. No. 12/323,183, filed Nov. 25, 2008, 9 pages.

International Search Report mailed on May 20, 2009, for PCT Application No. PCT/US2007/083638, filed on Nov. 5, 2007, 5 pages.

International Search Report mailed on Jul. 8, 2009, for PCT Application No. PCT/US2008/054354, filed Feb. 20, 2008, 8 pages.

International Search Report mailed on Aug. 4, 2008 for PCT Patent Application No. PCT/US2008/065666, filed Jun. 3, 2008, 3 pages.

International Search Report mailed on Jun. 26, 2009, for PCT Application No. PCT/US2009/033596, filed Feb. 9, 2009, 6 pages.

International Search Report mailed on Apr. 27, 2010, for PCT Patent Application No. PCT/US2010/026450, filed Mar. 5, 2010, 1 page.

Non-Final Office Action mailed on Sep. 23, 2010, for U.S. Appl. No. 12/513,491, filed Nov. 5, 2007, 10 pages.

Non-Final Office Action mailed on Oct. 21, 2010, for U.S. Appl. No. 11/778,498, filed Jul. 16, 2007, 18 pages.

Written Opinion of the International Searching Authority mailed on May 20, 2009, for PCT Patent Application No. PCT/US2007/083638, filed Nov. 5, 2007, 6 pages.

Written Opinion of the International Searching Authority mailed on Jul. 8, 2009, for PCT Patent Application No. PCT/US2008/054354, filed Feb. 20, 2008, 10 pages.

Written Opinion of the International Searching Authority mailed on Aug. 4, 2008, for PCT Patent Application No. PCT/US2008/065666, filed Jun. 3, 2008, 7 pages.

Written Opinion of the International Searching Authority mailed on Jun. 26, 2009, for PCT Patent Application No. PCT/US2009/033596, filed Feb. 9, 2009, 6 pages.

Written Opinion of the International Searching Authority mailed on Apr. 27, 2010, for PCT Patent Application No. PCT/US2010/026450, filed Mar. 5, 2010, 6 pages.

Amendment in Response to Non-Final Office Action submitted on Jan. 14, 2011, for U.S. Appl. No. 12/368,242, filed Feb. 9, 2009, 19 pages.

Amendment in Response to Non-Final Office Action submitted on Mar. 21, 2011, for U.S. Appl. No. 11/778,498, filed Jul. 16, 2007, 21 pages.

Extended European Search Report mailed on Feb. 28, 2011, for EP Patent Application No. 1152879.0, filed Oct. 10, 2006, 6 pages.

Extended European Search Report mailed on Mar. 2, 2011, for EP Patent Application No. 11152889.9, filed Oct. 10, 2006, 6 pages.

Extended European Search Report mailed on Mar. 22, 2011, for EP Patent Application No. 11152743.7, filed Feb. 9, 2007, 11 pages.

Final Office Action mailed on Jun. 9, 2011, for U.S. Appl. No. 12/513,491, filed Nov. 5, 2007 (Int'l. filing date), 10 pages.

Final Office Action mailed on Jun. 13, 2011, for U.S. Appl. No. 11/778,498, filed Jul. 16, 2007, 13 pages.

Non-Final Office Action mailed on Jul. 16, 2010, for U.S. Appl. No. 12/368,242, filed Feb. 9, 2009, 12 pages.

Non-Final Office Action mailed on Apr. 22, 2011, for U.S. Appl. 12/527,692, filed Feb. 20, 2008 (Int'l. filing date), 7 pages.

Notice of Allowance mailed on Mar. 4, 2011, for U.S. Appl. No. 12/368,242, filed Feb. 9, 2009, 5 pages.

\* cited by examiner

MAXILLOFACIAL BONE AUGMENTATION USING RHPDGF-BB AND A BIOCOMPATIBLE MATRIX

CROSS REFERENCE TO RELATED APPLICATIONS

This application is a continuation-in-part of application Ser. No. 11/159,533, filed Jun. 23, 2005, which is a continuation-in-part of application Ser. No. 10/965,319, filed Oct. 14, 2004, now abandoned. This application also claims the benefit of U.S. Provisional Patent Application No. 60/738,076, filed Nov. 17, 2005.

FIELD OF THE INVENTION

The present invention comprises compositions and methods for maxillofacial bone augmentation using compositions comprising a solution of PDGF and a biocompatible matrix, optionally including a biocompatible binder.

BACKGROUND OF THE INVENTION

Maxillofacial bone augmentation is needed in many situations including alveoar ridge augmentation (including horizontal and vertical ridge augmentation, in extraction sockets, in repair of bone sockets and deficiencies in the bony wall of the maxillary sinus.

Guided bone regeneration (GBR) is a regenerative procedure derived from guided tissue regeneration (GTR) around natural teeth and used for ridge augmentation prior to or in conjunction with osseointegrated implant placement. Originally, the biological principle of guided tissue regeneration was discovered by Nyman and Karring in the early 1980's. The surgical technique involves the placement of a cell occlusive barrier membrane to protect the blood clot and to create a secluded space around the bone defect to allow bone regeneration without competition from other tissues.

Schenk et al. (*Int. J. Oral Maxillofac. Implants* 1994; 9(1); 13-29) demonstrated how the newly regenerated bone progresses in a programmed sequence through a series of biological steps that closely parallel the pattern of normal bone growth and development. These findings have been confirmed by Simion et al. (*Clin. Oral Implants Res.* 1999; 10(2):73-84) with the same canine model using polytetrafluoroethylene (ePTFE) titanium-reinforced membranes. Evidence emerging from clinical studies also suggests that regenerated bone is capable of withstanding the occlusal loading exerted by functional forces, and is hence stable over time. (Mayfield et al. (*Clin. Oral Implants Res.* 1998; 9(5)297-302)).

GBR is well documented and studies demonstrate its high efficacy and predictability in horizontal and vertical ridge augmentation procedures. This last procedure, which is believed to be the most technically demanding of all GBR techniques, was first proposed by Simion et al. (*Int. J. Periodontic Restorative Dent.* 1994; 14(6):496:511) in 1994. It is indicated when bone height is insufficient for implant placement, long-term stability, or when prosthetic rehabilitation will result in excessively long crowns and an unfavorable implant/crown ratio.

A variety of materials are available for bone substitutes and membranes when applying the GBR principles. Human clinical studies have shown the possibility of successful vertical bone augmentation using e-PTFE membranes in combination with filling materials (autogenous bones (Tinti, et al., *Int. J. Periodontics Restorative Dent.* 1996; 16(3):220-9, Tinti, et al., *Int. J. Periodontics Restorative Dent.* 1998; 18(5):434-43)) and demineralized freeze-dried bone allograft (DFDBA), (Simion, et al., *Int. J. Periodontics Restorative Dent.* 1998; 18(1):8-23)).

One of the major issues concerning alveolar ridge augmentation procedures is the premature membrane exposure due to soft tissue dehiscence resulting in local infection and incomplete bone regeneration, jeopardizing the final results. In order to overcome these problems, the materials used and the surgical techniques applied in GBR have frequently been modified and adapted (Simion et al., *Int. J. Periodontics Restorative Dent.* 1994; 14(2):166-80, Simion et al, *J. Clin. Periodontol.* 1995; 22(4); 321-31).

Vertical ridge augmentation is needed for both the mandible and maxilla. Accordingly, what is needed are new methods and materials that are free of problems associated with prior art methods, and that are effective in augmenting bone, particularly augmentation maxillofacial bones, and particularly the alveolar ridge so that stable osseointegrated implants may be achieved.

SUMMARY OF THE INVENTION

The present invention provides effective new methods and compositions for bone augmentation, especially maxillofacial bone augmentation, that are free of problems associated with prior art methods. Such methods include, but are not limited to bone augmentation in the maxilla or mandible. Such bone augmentation sites may include but are not limited to alveolar ridge augmentation, repair of extraction sockets, sinus elevation, and deficiencies in the maxilla adjacent to the maxillary sinus. Alveolar ridge augmentation is one embodiment of the present invention and includes horizontal (lateral) and vertical ridge augmentation.

The compositions used in these methods include platelet derived growth factor (PDGF), such as recombinant human platelet derived growth factor (rhPDGF), a biocompatible matrix and, optionally, a resorbable membrane. The use of these compositions in the present method is effective in regenerating bone and in facilitating achievement of stable osseointegrated implants. While any bone may be augmented with the present invention, the mandible and maxilla are preferred bones for augmentation. Augmentation of alveolar ridges in the mandible and/or the maxilla is a preferred embodiment of the present invention.

In one aspect, a composition provided by the present invention for promoting bone augmentation comprises a solution comprising PDGF and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. The concentration of PDGF within the solution may be within any of the concentration ranges stated above.

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF such as rhPDGF-BB.

In some embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516, 896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a preferred embodiment, the rhPDGF-BB comprises at least 65% of the entire amino acid sequence of rhPDGF-B (1-109).

A biocompatible matrix, according to some embodiments of the present invention, comprises a bone scaffolding material, such as a bone block. In some embodiments, the bone block may be demineralized. In some embodiments, a bone scaffolding material comprises calcium phosphate. Calcium phosphate, in one embodiment, comprises β-tricalcium phosphate.

In another aspect, the present invention provides a composition for promoting bone augmentation procedure comprising a PDGF solution disposed in a biocompatible matrix, wherein the biocompatible matrix comprises a bone block and a biocompatible binder. The PDGF solution may have a concentration of PDGF as described above. A bone scaffolding material, in some embodiments, comprises calcium phosphate. In an embodiment, calcium phosphate comprises β-tricalcium phosphate.

Moreover, a biocompatible binder, according to some embodiments of the present invention, comprises proteins, polysaccharides, nucleic acids, carbohydrates, synthetic polymers, or mixtures thereof. In one embodiment, a biocompatible binder comprises collagen. In another embodiment, a biocompatible binder comprises hyaluronic acid.

In another aspect, the present invention provides a kit comprising a biocompatible matrix in a first package and a solution comprising PDGF in a second package. In some embodiments, the solution comprises a predetermined concentration of PDGF. The concentration of the PDGF can be predetermined according to the surgical procedure being performed. Moreover, in some embodiments, the biocompatible matrix can be present in the kit in a predetermined amount. The amount of biocompatible matrix provided by a kit can be dependent on the surgical procedure being performed. In some embodiments, the second package containing the PDGF solution comprises a syringe. A syringe can facilitate disposition of the PDGF solution in the biocompatible matrix for application at a surgical site, such as a site of bone fusion in a bone augmentation procedure. In some embodiments, the kit contains a resorbable membrane which may be used in the methods of the present invention.

The present invention additionally provides methods for producing compositions for use in bone augmentation procedures as well as methods of performing bone augmentation procedures. In one embodiment, a method for producing a composition comprises providing a solution comprising PDGF, providing a biocompatible matrix, and disposing the solution in the biocompatible matrix.

In another embodiment, a method of performing a bone augmentation procedure comprises providing a composition comprising a PDGF solution disposed in a biocompatible matrix and applying the composition to at least one site of desired bone augmentation. In some embodiments, the method comprises augmentation of the alveolar ridge of the mandible or maxilla. The augmented alveolar ridge may be prepared subsequently to receive an osseointegrated implant.

Accordingly, it is an object of the present invention to provide compositions comprising PDGF in a biocompatible matrix useful in facilitating bone augmentation.

It is an object of the present invention to provide compositions comprising PDGF in a biocompatible matrix useful in facilitating maxillofacial bone augmentation.

It is another object of the present invention to provide compositions comprising PDGF in a biocompatible matrix useful in facilitating bone augmentation in the maxilla or mandible.

Yet another object of the present invention is to provide compositions comprising PDGF in a biocompatible matrix useful in facilitating bone augmentation in the maxilla or mandible so that an implant may be inserted into the maxilla or mandible.

Another object of the present invention is to provide compositions comprising PDGF in a biocompatible matrix useful in facilitating alveolar ridge augmentation in the maxilla or mandible so that an implant may be stably inserted into the maxilla or mandible.

It is another object of the present invention to provide a method for vertical or horizontal bone augmentation, particularly in the maxilla and/or mandible.

Yet another object of the present invention is to provide a method for augmenting the alveolar ridge in the maxilla or mandible.

Another object of the present invention is to provide kits containing PDGF and a biocompatible matrix, optionally including a resorbable membrane.

These and other embodiments of the present invention are described in greater detail in the detailed description which follows. These and other objects, features, and advantages of the present invention will become apparent after review of the following detailed description of the disclosed embodiments and claims.

DETAILED DESCRIPTION

Figure 1:
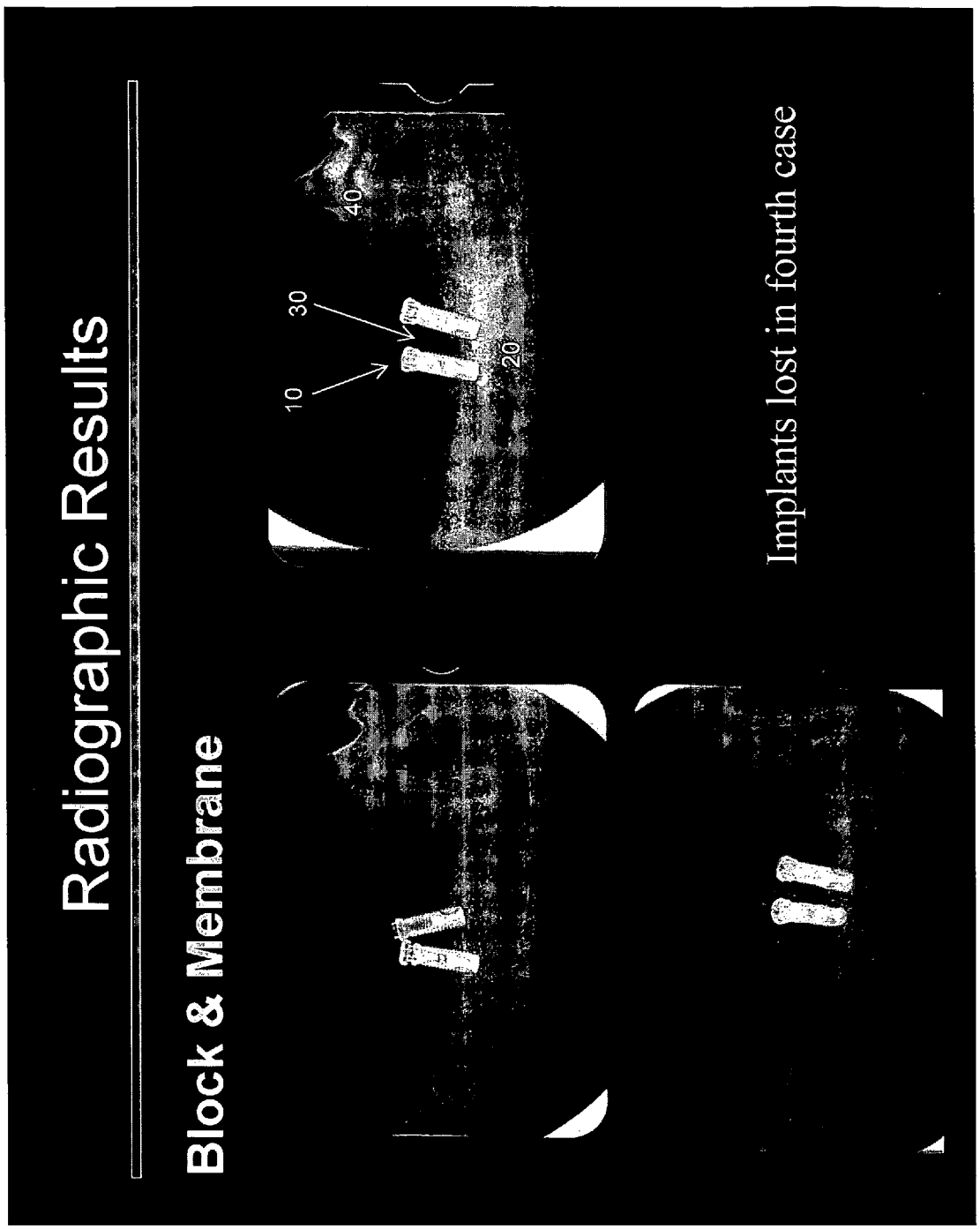
FIG. 1 presents radiographic results in 3 control animals receiving the deproteinized bovine block without PDGF, wherein the block was covered with the resorbable collagen membrane. The white, radiodense titanium implants (10) are placed in the mandible (20). The area (30) between the titanium implants is radiolucent and shows little or no bone growth. A nearby tooth (40) is shown.

The present invention provides effective new methods and compositions for bone augmentation, especially maxillofacial bone augmentation, that are free of problems associated with prior art methods. Such methods include, but are not limited to bone augmentation in the maxilla or mandible. Such bone augmentation sites may include but are not limited to alveolar ridge augmentation, repair of extraction sockets, sinus elevation, and deficiencies in the maxilla adjacent to the maxillary sinus. Alveolar ridge augmentation is one preferred embodiment of the present invention and includes horizontal (lateral) and vertical ridge augmentation. The term horizontal ridge is equivalent to lateral ridge and includes buccal, lingual and palatal ridges. The term vertical ridge includes the mandibular and maxillary vertical alveolar ridges.

In one embodiment, a composition for bone augmentation comprises a solution comprising PDGF and a biocompatible matrix, wherein the solution is disposed in the biocompatible matrix. In another embodiment, a composition comprises a PDGF solution disposed in a biocompatible matrix, wherein the biocompatible matrix comprises a bone scaffolding material and a biocompatible binder. In one embodiment PDGF is rhPDGF-BB in an acetate solution.

The present invention also provides a kit comprising a biocompatible matrix in a first package and a solution comprising PDGF in a second package which may act as a dispensing means. In some embodiments, the solution comprises a predetermined concentration of PDGF. In some embodiments, the concentration of PDGF is consistent with the values provided herein. The concentration of the PDGF can be predetermined according to the surgical procedure being performed. Moreover, in some embodiments, the biocompatible matrix can be present in the kit in a predetermined amount. The amount of biocompatible matrix provided by a kit can be dependent on the surgical procedure being performed. In specific embodiments the biocompatible matrix is a bone block or β-tricalcium phosphate. In some embodiments, the second package containing the PDGF solution comprises a dispensing means, such as a syringe. A syringe can facilitate disposition of the PDGF solution in the biocompatible matrix for application at a surgical site, such as a site of desired bone augmentation. In another embodiment, the kit also contains a resorbable membrane in another container.

Turning now to components that can be included in various embodiments of the present invention, compositions of the present invention comprise a solution comprising PDGF.

PDGF

PDGF plays an important role in regulating cell growth and division. PDGF, as with other growth factors, is operable to bind with the extracellular domains of receptor tyrosine kinases. The binding of PDGF to these transmembrane proteins switches on the kinase activity of their catalytic domains located on the cytosolic side of the membrane. By phosphorylating tyrosine residues of target proteins, the kinases induce a variety of cellular processes that include cell growth and extracellular matrix production.

In one aspect, a composition provided by the present invention comprises a solution comprising PDGF and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. PDGF may be present in the solution at any concentration within these stated ranges. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; or about 1.0 mg/ml. It is to be understood that these concentrations are simply examples of particular embodiments, and that the concentration of PDGF may be within any of the concentration ranges stated above.

Various amounts of PDGF may be used in the compositions of the present invention. Amounts of PDGF that could be used include amounts in the following ranges: about 1 ug to about 50 mg, about 10 ug to about 25 mg, about 100 ug to about 10 mg, and about 250 ug to about 5 mg. It is to be understood that the PDGF may be employed in conjunction with additional bone stimulating factors and/or drugs, for example bisphosphonates for inhibition of osteoclast activity.

The concentration of PDGF or other growth factors in embodiments of the present invention can be determined using methods known to one of ordinary skill in the art, for example by using an enzyme-linked immunoassay as described in U.S. Pat. Nos. 6,221,625, 5,747,273, and 5,290,708. Other assays known in the art may be used for determining PDGF concentration. When provided herein, the molar concentration of PDGF is determined based on the molecular weight (MW) of PDGF dimer (e.g., PDGF-BB; MW about 25 kDa).

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In one embodiment, PDGF comprises PDGF-BB. In another embodiment PDGF comprises a recombinant human (rh) PDGF, such as rhPDGF-BB.

PDGF, in some embodiments, can be obtained from natural sources. In other embodiments, PDGF can be produced by recombinant DNA techniques. In other embodiments, PDGF or fragments thereof may be produced using peptide synthesis techniques known to one of ordinary skill in the art, such as solid phase peptide synthesis. When obtained from natural sources, PDGF can be derived from biological fluids. Biological fluids, according to some embodiments, can comprise any treated or untreated fluid associated with living organisms including blood Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available GMP recombinant PDGF-BB can be obtained commercially from Chiron Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.).

In some embodiments of the present invention, PDGF comprises PDGF fragments. In one embodiment rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a preferred embodiment, the rhPDGF-BB comprises at least 65% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In one embodiment, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of platelet rich plasma (PRP), fresh frozen plasma (FFP), or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. Nos. 10/965,319 and 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino) propanesulfonic acid (MOPS). Buffers can be selected based on biocompatibility with PDGF and the buffer's ability to impede undesirable protein modification. Buffers can additionally be selected based on compatibility with host tissues. In a preferred embodiment, sodium acetate buffer is used. The buffers may be employed at different molarities, for example about 0.1 mM to about 100 mM, about 1 mM to about 50 mM, about 5 mM to about 40 mM, about 10 mM to about 30 mM, or about 15 mM to about 25 mM, or any molarity within these ranges. In one embodiment, an acetate buffer is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In one embodiment, a solution comprising PDGF has a pH ranging from about 5.0 to about 8.0, more preferably about 5.5 to about 7.0, most preferably about 5.5 to about 6.5, or any value within these ranges. The pH of solutions comprising PDGF, in some embodiments, can be compatible with the prolonged stability and efficacy of PDGF or any other desired biologically active agent. PDGF is generally more stable in an acidic environment. Therefore, in accordance with one embodiment the present invention comprises an acidic storage formulation of a PDGF solution. In accordance with this embodiment, the PDGF solution preferably has a pH from about 3.0 to about 7.0, and more preferably from about 4.0 to about 6.5. The biological activity of PDGF, however, can be optimized in a solution having a neutral pH range. Therefore, in a further embodiment, the present invention comprises a neutral pH formulation of a PDGF solution. In accordance with this embodiment, the PDGF solution preferably has a pH from about 5.0 to about 8.0, more preferably about 5.5 to about 7.0, most preferably about 5.5 to about 6.5. In accordance with a method of the present invention, an acidic PDGF solution is reformulated to a neutral pH composition, wherein such composition is then used to treat bone in order to promote growth. In accordance with a preferred embodiment of the present invention, the PDGF utilized in the solutions is rhPDGF-BB.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components. In other embodiments, solutions comprising PDGF can further comprise cell culture media, other stabilizing proteins such as albumin, antibacterial agents, protease inhibitors (e.g., EDTA, EGTA, aprotinin, EACA, etc.) and/or other growth factors such as FGFs, EGF, TGFs, KGFs, IGFs BMPs, or other PDGFs including PDGF-AA, PDGF-BB, PDGF-AB, PDGF-CC and/or PDGF-DD.

In addition to solutions comprising PDGF, compositions of the present invention also comprise a biocompatible matrix in which to dispose the PDGF solutions and may also comprise a biocompatible binder either with or without addition of a biocompatible matrix.

Biocompatible Matrix

Bone Scaffolding Material

A biocompatible matrix, according to embodiments of the present invention, comprises a bone scaffolding material. The bone scaffolding material provides the framework or scaffold for new bone and tissue growth to occur.

A bone scaffolding material, in some embodiments, comprises a bone block. Bone blocks may be obtained from different sources. In one embodiment, a deproteinized bovine bone block is used (Bio-Oss Block, Geistlich biomaterials). Deproteinized bovine bone is a xenogenic material processed to remove the organic component. Its efficacy has been well demonstrated both in periodontal and implant literature in terms of long-term stability (Sarton et al., *Clin Oral implants Res.* 2003 June: 14(3):369-72). Deproteinized bone may be obtained from other species, including but not limited to humans, and used in the present invention.

Other matrix materials may be used in the present invention, such as autologous cortical, cancellous and cortico-cancellous bone blocks and particulate graft having an average diameter of 0.1 mm to 100 mm. Further, allogeneic, xenogenic, cortical, cancellous and cortico-cancellous bone blocks and pieces having an average diameter of 0.1 mm to 100 mm may also be used in the present invention.

In some embodiments, a bone scaffolding material comprises porous structure. Porous bone scaffolding materials, according to some embodiments, can comprise pores having diameters ranging from about 1 μm to about 1 mm. In one embodiment, a bone scaffolding material comprises macropores having diameters ranging from about 100 μm to about 1 mm. In another embodiment, a bone scaffolding material comprises mesopores having diameters ranging from about 10 μm to about 100 μm. In a further embodiment, a bone scaffolding material comprises micropores having diameters less than about 10 μm. Embodiments of the present invention contemplate bone scaffolding materials comprising macropores, mesopores, and micropores or any combination thereof.

A porous bone scaffolding material, in one embodiment, has a porosity greater than about 25%. In another embodiment, a porous bone scaffolding material has a porosity greater than about 50%. In a further embodiment, a porous bone scaffolding material has a porosity greater than about 90%.

A bone scaffolding material, in some embodiments, comprises at least one calcium phosphate. In other embodiments, a bone scaffolding material can comprise a plurality of calcium phosphates. Calcium phosphates suitable for use as a bone scaffolding material, in embodiments of the present invention, have a calcium to phosphorus atomic ratio ranging from 0.5 to 2.0.

Non-limiting examples of calcium phosphates suitable for use as bone scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-tricalcium phosphate, hydroxyapatite (OHAp), poorly crystalline hydroxapatite, tetracalcium phosphate (TTCP), heptacalcium decaphosphate, calcium metaphosphate, calcium pyrophosphate dihydrate, calcium pyrophosphate, carbonated calcium phosphate, or mixtures thereof.

In some embodiments, a bone scaffolding material comprises a plurality of particles. A bone scaffolding material, for example, can comprise a plurality of calcium phosphate particles. Bone scaffolding particles, in one embodiment, have an average diameter ranging from about 1 μm to about 5 mm. Bone scaffolding particles, in one embodiment, have an average diameter ranging from about 1 μm to about 2 mm. Bone scaffolding particles, in one embodiment, have an average diameter ranging from about 1 mm to about 2 mm. In other embodiments, particles have an average diameter ranging from about 250 μm to about 1000 μm. In other embodiments, particles have an average diameter ranging from about 250 μm to about 750 μm. Bone scaffolding particles, in another embodiment, have an average diameter ranging from about 100 μm to about 300 μm. Bone scaffolding particles, in another embodiment, have an average diameter ranging from about 100 μm to about 400 μm. In a further embodiment, the particles have an average diameter ranging from about 75 μm to about 300 μm. In additional embodiments, bone scaffolding particles have an average diameter less than about 1 μm and, in some cases, less than about 1 mm.

Bone scaffolding materials, according to some embodiments, can be provided in a shape suitable for implantation (e.g., a sphere, a cylinder, or a block). In other embodiments, bone scaffolding materials are moldable. Moldable bone scaffolding materials can facilitate efficient placement of compositions of the present invention in and around target sites in bone. In some embodiments, moldable bone scaffolding materials can be applied to sites of desired bone augmentation with a spatula or equivalent device. In some embodiments, bone scaffolding materials are flowable. Flowable bone scaffolding materials, in some embodiments, can be applied to sites of bone fusion through a syringe and needle or cannula. In some embodiments, bone scaffolding materials harden in vivo.

In some embodiments, bone scaffolding materials are bioresorbable. A bone scaffolding material, in one embodiment, can be resorbed within one year of in vivo implantation. In another embodiment, a bone scaffolding material can be resorbed within 1, 3, 6, or 9 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Bone Scaffolding Comprising β-Tricalcium Phosphate

A bone scaffolding material for use as a biocompatible matrix can comprise β-tricalcium phosphate (β-TCP). β-TCP, according to some embodiments, can comprise a porous structure having multidirectional and interconnected pores of varying diameters. The porous structure of β-TCP, in one embodiment, comprises macropores having diameters ranging from about 100 μm to about 1 mm, mesopores having diameters ranging from about 10 μm to about 100 μm, and micropores having diameters less than about 10 μm. Macropores and micropores of the β-TCP can facilitate osteoinduction and osteoconduction while macropores, mesopores and micropores can permit fluid communication and nutrient transport to support bone regrowth throughout the β-TCP biocompatible matrix.

In comprising a porous structure, β-TCP, in some embodiments, can have a porosity greater than 25%. In other embodiments, β-TCP can have a porosity greater than 50%. In a further embodiment, β-TCP can have a porosity greater than 90%.

In some embodiments, a bone scaffolding material comprises β-TCP particles. β-TCP particles, in one embodiment, have an average diameter ranging from about 1 μm to about 5 mm. β-TCP particles, in one embodiment, have an average diameter ranging from about 1 μm to about 2 mm. β-TCP particles, in one embodiment, have an average diameter ranging from about 1 mm to about 2 mm. In other embodiments, β-TCP particles have an average diameter ranging from about 250 μm to about 1000 μm. In other embodiments, β-TCP particles have an average diameter ranging from about 250 μm to about 750 μm. In another embodiment, β-TCP particles have an average diameter ranging from about 100 μm to about 400 μm. In another embodiment, β-TCP particles have an average diameter ranging from about 100 μm to about 300 μm. In a further embodiment, β-TCP particle have an average diameter ranging from about 75 μm to about 300 μm. In additional embodiments, β-TCP particles have an average diameter less than 25 μm and, in some cases, an average diameter less than 1mm. In additional embodiments, β-TCP particles have an average diameter less than 1 μm and, in some cases, an average diameter less than 1 mm.

A biocompatible matrix comprising a β-TCP bone scaffolding material, in some embodiments, can be provided in a shape suitable for implantation (e.g., a sphere, a cylinder, or a block). In other embodiments, a β-TCP bone scaffolding material can be moldable thereby facilitating placement of the matrix in sites of desired bone augmentation such as the maxilla or mandible. Flowable matrices may be applied through syringes, tubes, or spatulas.

A β-TCP bone scaffolding material, according to some embodiments, is bioresorbable. In one embodiment, a β-TCP bone scaffolding material can be at least 75% resorbed one year subsequent to in vivo implantation. In another embodiment, a β-TCP bone scaffolding material can be greater than 90% resorbed one year subsequent to in vivo implantation.

Bone Scaffolding Material and Biocompatible Binder

In another embodiment, a biocompatible matrix comprises a bone scaffolding material and a biocompatible binder. Bone scaffolding materials in embodiments of a biocompatible matrix further comprising a biocompatible binder are consistent with those provided hereinabove.

Biocompatible binders, according to some embodiments, can comprise materials operable to promote cohesion between combined substances. A biocompatible binder, for example, can promote adhesion between particles of a bone scaffolding material in the formation of a biocompatible matrix. In certain embodiments, the same material may serve as both a scaffolding material and a binder if such material acts to promote cohesion between the combined substances and provides a framework for new bone growth to occur.

Biocompatible binders, in some embodiments, can comprise collagen, collagen of various degrees of cross-linking, polysaccharides, nucleic acids, carbohydrates, proteins, polypeptides, poly(α-hydroxy acids), poly(lactones), poly (amino acids), poly(anhydrides), poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polyurethanes, polymethylmethacrylate, carbon fibers, poly(ethylene glycol), poly (ethylene oxide), poly(vinyl alcohol), poly (vinylpyrrolidone), poly(ethyloxazoline), poly(ethylene oxide)-co-poly(propylene oxide) block copolymers, poly (ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, lecithin, N,O-carboxymethyl chitosan, phosphatidylcholine derivatives, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, a pluronic acid, sodium glycerophosphate, glycogen, a keratin, silk, and derivatives and mixtures thereof, and binders known to one of ordinary skill in the art for use in orthopedic applications.

In some embodiments, a biocompatible binder is water-soluble. A water-soluble binder can dissolve from the biocompatible matrix shortly after its implantation, thereby introducing macroporosity into the biocompatible matrix. Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 5 weight percent to about 50 weight percent of the matrix. In other embodiments, a biocompatible binder can be present in an amount ranging from about 10 weight percent to about 40 weight percent of the biocompatible matrix. In another embodiment, a biocompatible binder can be present in an amount ranging from about 15 weight percent to about 35 weight percent of the biocompatible matrix. In a further embodiment, a biocompatible binder can be present in an amount of about 20 weight percent of the biocompatible matrix.

A biocompatible matrix comprising a bone scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in one embodiment, can comprise particles of a bone scaffolding material adhered to one another by a biocompatible binder.

A biocompatible matrix in paste or putty form can be molded into the desired implant shape or can be molded to the contours of the implantation site. In one embodiment, a biocompatible matrix in paste or putty form can be injected into an implantation site with a syringe or cannula.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a bone scaffolding material and a biocompatible binder, in some embodiments, can also be provided in a predetermined shape including a block, sphere, or cylinder or any desired shape, for example a shape defined by a mold or a site of application.

A biocompatible matrix comprising a bone scaffolding material and a biocompatible binder, in some embodiments, is bioresorbable. A biocompatible matrix, in such embodiments, can be resorbed within one year of in vivo implantation. In another embodiment, a biocompatible matrix comprising a bone scaffolding material and a biocompatible binder can be resorbed within 1, 3, 6, or 9 months of in vivo implantation. Bioresorbablity will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Biocompatible Matrix Comprising β-TCP and Collagen

In some embodiments, a biocompatible matrix can comprise a β-TCP bone scaffolding material and a biocompatible collagen binder. β-TCP bone scaffolding materials suitable for combination with a collagen binder are consistent with those provided hereinabove.

A collagen binder, in some embodiments, can comprise any type of collagen, including Type I, Type II, and Type III collagens. The collagen used may also be cross-linked to various extents. In one embodiment, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, can comprise a plurality of β-TCP particles adhered to one another with a collagen binder. In one embodiment, β-TCP particles suitable for combination with a collagen binder have an average diameters as described above.

β-TCP particles, in some embodiments, can be adhered to one another by the collagen binder so as to produce a biocompatible matrix having a porous structure. In some embodiments, a biocompatible matrix comprising β-TCP particles and a collagen binder can comprise pores having diameters ranging from about 1 μm to about 1 mm. A biocompatible matrix comprising β-TCP particles and a collagen binder can comprise macropores having diameters ranging from about 100 μm to about 1 mm, mesopores having diameters ranging from about 10 μm to 100 μm, and micropores having diameters less than about 10 μm.

A biocompatible matrix comprising β-TCP particles and a collagen binder can have a porosity greater than about 25%. In another embodiment, the biocompatible matrix can have a porosity greater than about 50%. In a further embodiment, the biocompatible matrix can have a porosity greater than about 90%.

A biocompatible matrix comprising β-TCP particles, in some embodiments, can comprise a collagen binder in an amount ranging from about 5 weight percent to about 50 weight percent of the matrix. In other embodiments, a collagen binder can be present in an amount ranging from about 10 weight percent to about 40 weight percent of the biocompatible matrix. In another embodiment, a collagen binder can be present in an amount ranging from about 15 weight percent to about 35 weight percent of the biocompatible matrix. In a further embodiment, a collagen binder can be present in an amount of about 20 weight percent of the biocompatible matrix.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In one embodiment, a biocompatible matrix in paste or putty form comprising β-TCP particles and a collagen binder can be injected into an implantation site with a syringe or cannula.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In one embodiment, a biocompatible matrix comprising β-TCP particles and a collagen binder can be at least 75% resorbed one year subsequent to in vivo implantation. In another embodiment, a biocompatible matrix comprising β-TCP particles and a collagen binder can be greater than 90% resorbed one year subsequent to in vivo implantation.

A solution comprising PDGF can be disposed in a biocompatible matrix to produce a composition for promoting bone augmentation, particularly of the vertical alveolar ridge according to embodiments of the present invention.

Resorbable Membrane

In order to improve treatment outcome and predictability of GBR procedures, complications encountered in such procedures should be reduced or eliminated. One of the observed and most threatening negative outcomes that may occur is early membrane exposure with bacterial contamination resulting in failure or incomplete success of GBR procedure (Simion et al., Int. J. Periodontics Restorative Dent. 1994; 14(2):166-80, Simion et al., J. Clin Periodontol. 1995; 22(4): 321-31, Simion et al., Clin. Oral Implants Res. 1997; 8(1): 23-31). This is particularly evident when using non-resorbable membranes, e.g. GORE-TEX®. The main advantage in using these membranes is the possibility to keep them in situ for the needed time period for the healing process to occur. Resorbable membranes made, for example, of natural or synthetic polymers such as collagen or polylactides and/or polyglycolides may also be used. These membranes have the advantage of gradually absorbing over time thus eliminating the need to surgically remove them. In the present investigation described in Example 1, collagen membranes were used. These membranes must be wetted in order to conform properly to the surgical site. The results in Example 1 showed no difference in bone augmentation surrounding the titanium implants between animals receiving bovine blocks with PDGF and animals receiving bovine blocks with PDGF and the collagen resorbable membrane. Accordingly, resorbable membranes may optionally be employed in the practice of the present invention.

Disposing PDGF Solution in a Biocompatible Matrix

The present invention provides methods for producing compositions for use in bone augmentation procedures. In one embodiment, a method for producing a composition for promoting the fusion of bone comprises providing a solution comprising PDGF, providing a biocompatible matrix, and disposing the solution in the biocompatible matrix. PDGF solutions and biocompatible matrices suitable for combination are consistent with those described hereinabove.

In one embodiment, a PDGF solution can be disposed in a biocompatible matrix by soaking the biocompatible matrix in the PDGF solution. A PDGF solution, in another embodiment, can be disposed in a biocompatible matrix by injecting the biocompatible matrix with the PDGF solution. In some embodiments, injecting a PDGF solution can comprise disposing the PDGF solution in a syringe and expelling the PDGF solution into the biocompatible matrix to saturate the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can already demonstrate a flowable paste or putty form prior to receiving a solution comprising PDGF.

Compositions Further Comprising Biologically Active Agents

Compositions for promoting and/or facilitating bone augmentation, according to some embodiments, can further comprise one or more biologically active agents in addition to PDGF. Biologically active agents that can be incorporated into compositions of the present invention in addition to PDGF can comprise organic molecules, inorganic materials, proteins, peptides, nucleic acids (e.g., genes, gene fragments, gene regulatory sequences, and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. Nos. 10/965,319 and 11/159,533 (Publication No: 20060084602). Preferred biologically active compounds that can be incorporated into compositions of the present invention include osteoinductive factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, calcitonin mimetics, statins, statin derivatives, or parathyroid hormone. Preferred factors also include protease inhibitors, as well as osteoporotic treatments that decrease bone resorption including bisphosphonates, and antibodies to receptor activator of NF-kB ligand (RANK) ligand.

Standard protocols and regimens for delivery of additional biologically active agents are known in the art. Additional biologically active agents can be introduced into compositions of the present invention in amounts that allow delivery of an appropriate dosage of the agent to the implant site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition for promoting bone augmentation, according to some embodiments, can further comprise the addition of other bone grafting materials with PDGF including autologous bone marrow, autologous platelet extracts, and synthetic bone matrix materials.

Methods of Performing Bone Augmentation Procedures

The present invention also provides methods of performing bone augmentation procedures. In one embodiment, a method of performing a bone augmentation procedure comprises providing a composition comprising a PDGF solution disposed in a biocompatible matrix, and optionally containing a biocompatible binder, and applying the composition to at least one site of desired bone augmentation. In some embodiments, a method of performing a bone augmentation procedure comprises applying the composition to at least one site of bone augmentation in the maxilla or mandible. A composition comprising a PDGF solution disposed in a biocompatible matrix, for example, can be packed into a site of desired bone augmentation in the maxilla or mandible. In another embodiment, the PDGF solution is applied to the implantation site before, and optionally after placement of the composition comprising the PDGF solution disposed in the biocompatible matrix into the implantation site. By enhancing the deposition of bone in the maxilla or mandible, the alveolar ridge may be enhanced so as to subsequently receive an implant. Such implants may be used for a variety of purposes, including as a support for a tooth or other dental device, and for various oral and maxillofacial applications, including extraction sockets, sinus elevation, and ridge augmentation.

Kits

The present invention also provides a kit comprising a biocompatible matrix in a first container and a solution comprising PDGF in a second container which may act as a dispensing means. In some embodiments, the solution comprises a predetermined concentration of PDGF. In some embodiments, the concentration of PDGF is consistent with the values provided herein. The concentration of the PDGF can be predetermined according to the surgical procedure being performed. Moreover, in some embodiments, the biocompatible matrix can be present in the kit in a predetermined amount. The amount of biocompatible matrix provided in a kit can be dependent on the surgical procedure being performed. In some embodiments, the second package containing the PDGF solution comprises a dispensing means, such as a syringe or a compressible tube. A syringe or a compressible tube can facilitate disposition of the PDGF solution in the biocompatible matrix for application at a surgical site, such as a site of desired bone augmentation. In another embodiment, the kit also contains a bioresorbable membrane in another container. In one embodiment, the bioresorbable membrane comprises a collagen bioresorbable membrane.

In one embodiment, the kit contains a first container with a biocompatible matrix. In one embodiment the biocompatible matrix is calcium phosphate. In a preffered embodiment the biocompatible matrix is β-tricalcium phosphate. In another preferred embodiment the biocompatible matrix is a bone block, for example an xenogenic, autologous cortical, cancellous or cortico-cancellous bone blocks. Such bone blocks may be demineralized as described previously in this application. The allogeneic, xenogenic, cortical, cancellous and cortico-cancellous bone blocks and pieces placed in the first container may have an average diameter of 0.1 mm to 100 mm. The specific size of the bone block in the kit depends on the specific application.

The kit contains a second container comprising PDGF. In one embodiment, the PDGF may be present in a dry form, for example as a powder or a lyophilized form at a selected amount appropriate for use in augmenting bone. When PDGF is present in dry form, another container may be present in the kit containing the solution for solvation of the PDGF before application to the biocompatible matrix. In another embodiment, the PDGF may be present in solution as described previously in this application. This second container may take the form of a dispensing container, such as a syringe or a compressible tube, to facilitate delivery of the PDGF in solution to the biocompatible matrix. While the PDGF may be any PDGF, as recited earlier in this application, in a preferred embodiment the PDGF is PDGF-BB. In another preferred embodiment, the PDGF-BB is rhPDGF-BB. In a preferred embodiment the second container contains rhPDGF-BB in acetate solution of about 15 mM to about 25 mM, preferably about 20 mM, at a pH of about 5.5 to 6.5.

The amount of PDGF in the second container may change depending on the intended application. The total amount of PDGF in the second container may be about 1 ug to about 50 mg, about 10 ug to about 25 mg, about 100 ug to about 10 mg, and about 250 ug to about 5 mg, or any specific amount within these ranges. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml or any specific concentration within these ranges. In other embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; or about 1.0 mg/ml.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention. Example 1 describes a study of vertical ridge augmentation in the mandible of the dog. Example 2 describes a study describes a study of vertical ridge augmentation in the maxilla of humans.

EXAMPLE 1

Method of Vertical Ridge Augmentation in Dogs using rhPDGF-BB and a Deproteinized Bovine Bone Block Alone or in Conjunction with a Resorbable Membrane The principal aims of this study were: 1) To clinically and radiographically evaluate the potential of utilizing rhPDGF-BB and a deproteinized bovine bone block in conjunction with a resorbable membrane in vertical ridge augmentation; 2) To clinically and histologically evaluate the role of a resorbable membrane in bone regeneration mediated by rhPDGF-BB; 3) To evaluate clinically, radiographically and histologically the safety and efficacy of using rhPDGF and a bone block in the absence of membranes to treat vertical bone defects with regard to biocompatibility, osteoconductivity, osteoinductivity, degradability and substitution; 4) To analyze histologically the healing pattern in the test sites; and, 5) To evaluate the bone to implant contact (BIC) of the regenerated bone on two different implant surfaces.

Figure 2:
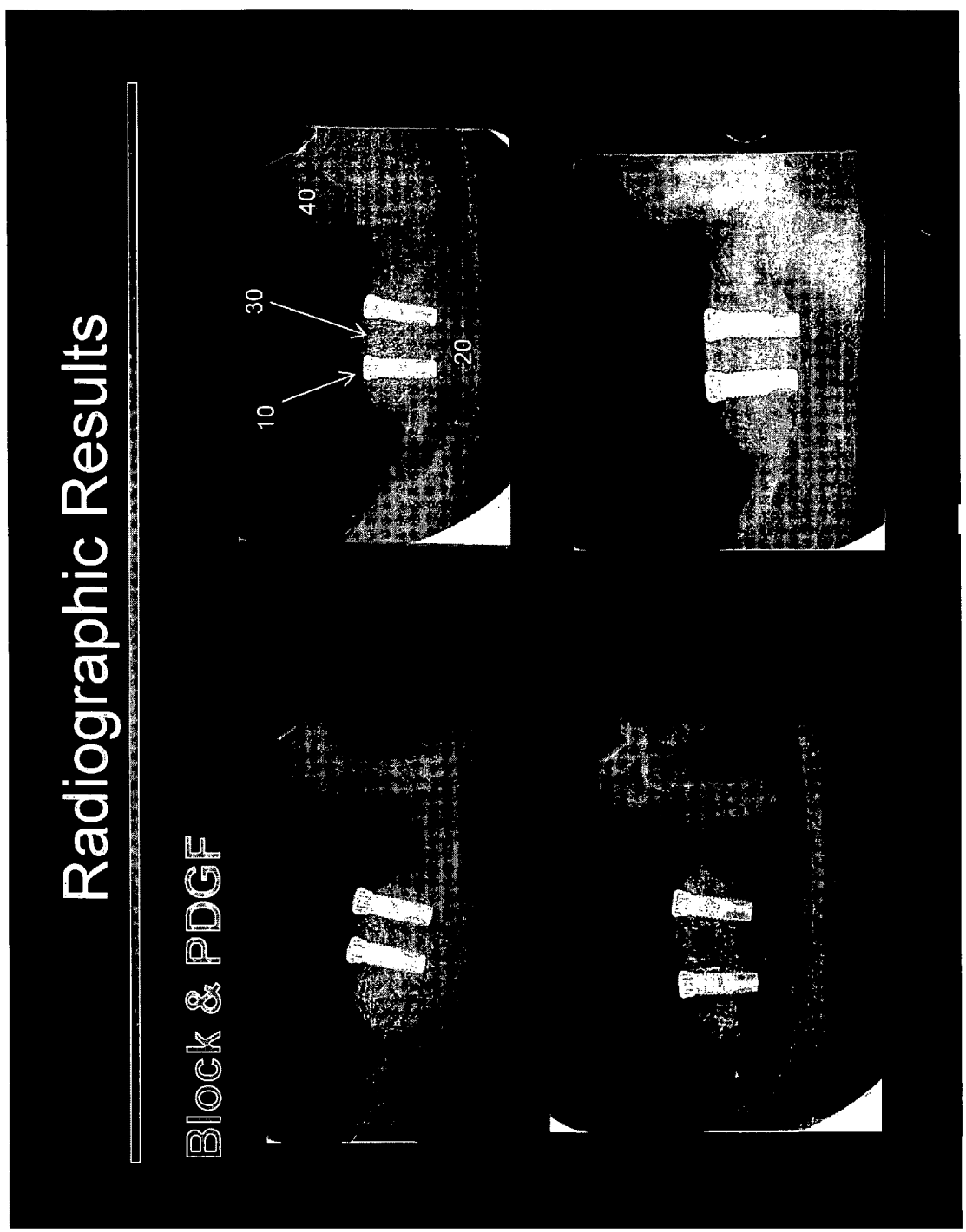
FIG. 2 presents radiographic results in 4 experimental animals receiving the deproteinized bovine block with PDGF. The white, radiodense titanium implants (10) are placed in the mandible (20). The area (30) between the titanium implants is relatively radiodense and shows bone growth. A nearby tooth (40) is shown.
Figure 3:
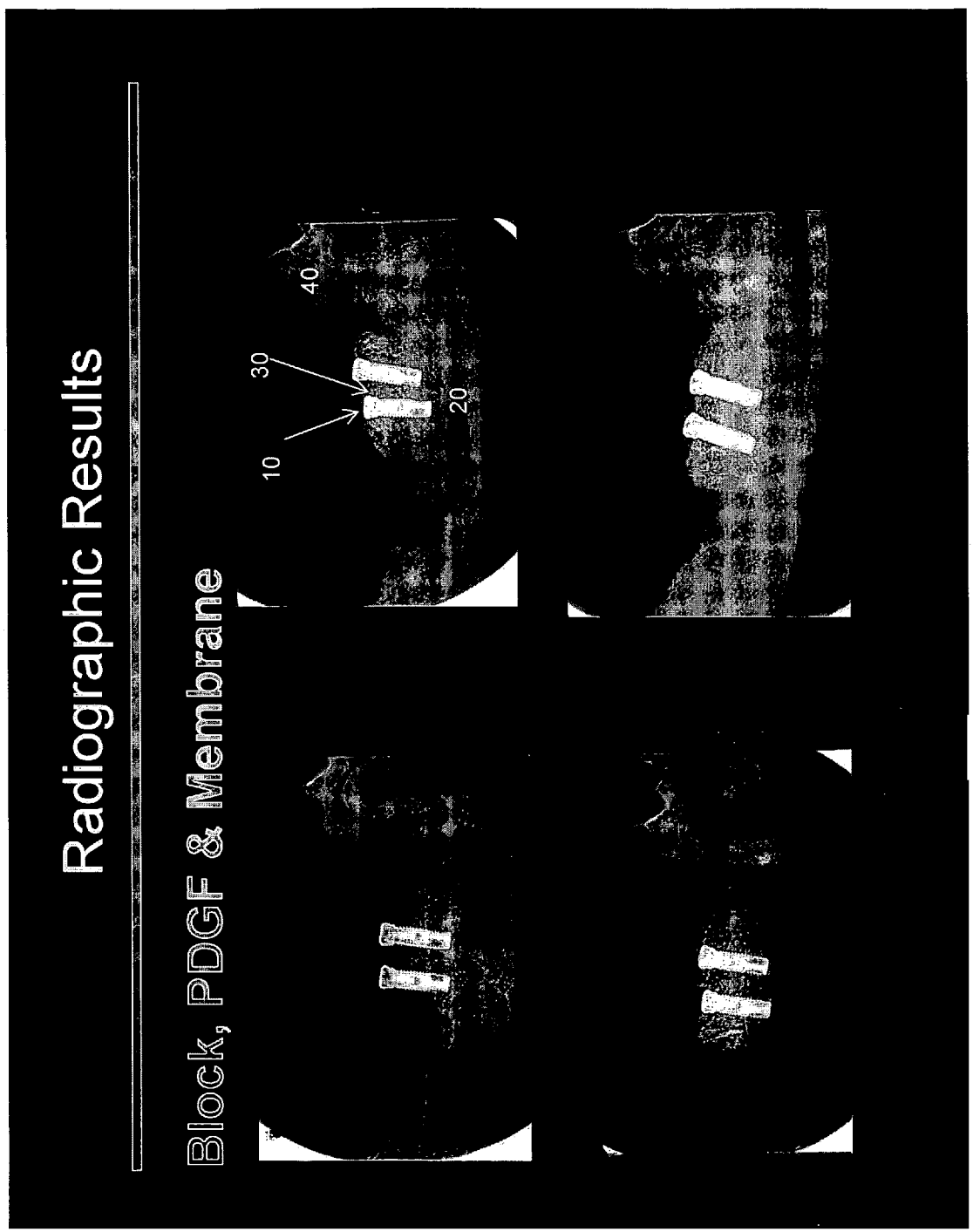
FIG. 3 presents radiographic results in 4 experimental animals receiving the deproteinized bovine block with PDGF, wherein the block was covered with the resorbable collagen membrane. The white radiodense titanium implants (10) are placed in the mandible (20). The area (30) between the titanium implants is relatively radiodense and shows bone growth. A nearby tooth (40) is shown.

This was an open-labeled, prospective, controlled study using the split-mouth method, comparing in the same animal, the clinical, radiographic and histological outcome in terms of vertical ridge augmentation in artificially created alveolar deficient ridges. The test sites were divided in three distinct groups, each of which was compared with each other.
GROUP 1: 4 sites received the combination of a deproteinized bovine bone block (Bio-Oss Block, Geistlich biomaterials), rhPDGF-BB (BioMimetic Therapeutics) and a resorbable membrane (Bio-Gide, Geistlich biomaterials) (FIG. 1).
GROUP 2: 4 sites received the combination of a deproteinized bovine bone block and rhPDGF-BB (FIG. 2).
GROUP 3: 4 sites received the combination of a deproteinized bovine bone block and a resorbable membrane (FIG. 3).

In addition, two titanium implants (Nobel Biocare, MKIII, 3.3×10 mm) were inserted (mesially and distally) at baseline in all sites. The two implants differed in surface characteristics being a Machined and a Ti-Unite. At 4 months post-op, a biopsy of the inserted implants with their surrounding tissue was extracted for examination.

The test sites were monitored by means of radiographic evaluation at the preliminary procedure, at baseline, and at the re-entry surgery.
Animal randomization: In order to evaluate each test group an equal number of times with every other one, the following combinations were applied. Two dogs were evaluated in each condition.

TABLE 1

Combinations Tested in Animals

| DOG | SIDE | |
|---|---|---|
| | RIGHT | LEFT |
| 1 | T1 | T2 |
| 2 | T1 | T2 |
| 3 | T1 | T3 |
| 4 | T1 | T3 |
| 5 | T2 | T3 |
| 6 | T2 | T3 |

T1: Bio Block + PDGF + Bio gide
T2: Bio Block + PDGF
T3: Bio Block + Bio gide
Two dogs received: T1 vs T2, two dogs received: T1 vs T3, and two dogs received: T2 vs T3.

Animal inclusion criteria: A total of 6 dogs satisfying the following inclusion criteria were included in the study: 1) Minimum age of 8-9 months in order to have reached the correct bone maturity; 2) Absence of primary dentition; and, 3) Weight at baseline >25 kg.
Experimental Procedures
Preliminary procedures. Oral prophylaxis utilizing hand and ultrasonic instrumentation was performed 2 weeks prior to baseline and 2 weeks prior to experimental procedures The following baseline measurements were performed after anesthesia: 1. Intraoral photographs of the defect area (optional); 2. Mesial-distal, bucco-lingual and apico-coronal dimensions of the bone defect; and, 3. Distance from the implant shoulder to the bone crest when inserted
Surgical Procedures (B1)
Baseline Procedure; Tooth Extraction and Creation of the Defect After achievement of general and local anesthesia, a radiographic evaluation was performed. An intrasulcular incision was traced in the posterior region of the mandible both in the right and the left side following the first bicuspid up to the first molar. A mesial releasing incision was traced mesial to the first bicuspid. A distal releasing incision was performed mesial to the first molar. A full thickness flap was elevated and the four premolars extracted. In the same area a vertical defect was artificially created by means of diamond burs along the posterior region of the mandible in order to mimic a deficient alveolar ridge. The defect had the following dimensions; 30 mm in a disto-mesial direction and 7 mm in an apico-coronal direction. The height depended on the topography of the inferior alveolar nerve. The width (bucco-lingual) was the full width of the mandible and thus varied somewhat depending upon the natural width of the animal's mandible. Flaps were sutured over the alveolar crest with interrupted 4/0 silk sutures. Animals were administered the standard post-surgical infection control (Amoxicillin clavulanic acid 2 gm/daily and nimesulide 100 mg every 12 hours for three days). A healing period of three months was required prior to the second surgery.
Second Surgical Procedure/Test Procedure; TI (4 sites)

After achievement of general and local anesthesia, a radiographic evaluation was performed. A crestal incision was traced from mesial to distal, extending distal to the first molar. The buccal and lingual/palatal flap was elevated full thickness to expose the alveolar crest. Excessive soft connective tissue was discarded. Cortical perforations were performed with a 2 mm diameter diamond round bur to expose the medullary spaces and allow bleeding. Intra-operative measurements were then taken. rhPDGF-BB (available in a liquid form) was added under suction to the bovine block in order for the block to become soaked due to its porous characteristics. This was performed by placing the bovine block in a 50 ml plastic sterile syringe, containing the liquid rhPDGF-BB to soak the permeable block under pressure. The block was left in the syringe filled with rhPDGF for approximately 10 minutes.

In the present investigation, a bone block of dimensions 2 cm×1 cm×1 cm was soaked in a solution of rhPDGF at a concentration of 0.3 mg/ml under suction using a large bore syringe. The theoretical void volume of the bone block was calculated as 1.56 ml Actual saturation of the block with a dye solution occurred at 1.67 ml. Accordingly, the total amount of rhPDGF in the block was about (0.3 mg/ml) (1.67 ml) =0.501 mg. During the surgery, these blocks were trimmed to fit within the bone defects so the final size may have varied by up to about 30% when compared to the original size.

In the present investigation, collagen membranes were used. These membranes must be wetted in order to conform properly to the surgical site. In this study, the collagen membranes were saturated with a solution containing 0.3 mg/ml of rhPDGF prior to implantation into the surgical site.

The bone was then placed onto the alveolar bone in the area of the residual bone defect, and stabilized by means of two titanium implants, which perforated the block first and next the cortical mandibular bone. The two titanium implants (Nobel Biocare, MKIII 3.3×10 mm, machined and Ti Unite) were inserted following the standard Branemark protocol in a distal and mesial position allowing a minimum distance of 10 mm between the two. Next, the resorbable membrane (Bio Gide, 30×40 mm) soaked in the rhPDGF solution was added to cover the filling materials and the implants.

It is to be understood that other attachment means may be employed as commonly known to one of ordinary skill in the art. In another embodiment, no attachment means are required when the block is press-fit into the recipient space.

The flaps were closed with internal horizontal mattress sutures prior to the interrupted sutures to ensure primary passive closure of the tissue. If closure was not achieved without further mobilization of the buccal flap, then the buccal full thickness flap was further extended in an apical direction by a periosteal incision. 5-0 Gore-Tex sutures were employed. Buccal and lingual photographs were taken following completion of flap closure in addition to a radiographic evaluation.

Test Procedure; T2 (4 sites)

The employed surgical technique was identical to the one described above (T1) except for the omission of the resorbable membrane.

Test Procedure; T3 (4 sites)

The employed surgical technique was identical to the one described above (T1) except for the omission of rhPDGF-BB.

Animal Sacrifice: (B2)

The six animals were sacrificed 4 months after the test (second) surgical procedure to allow the healing process to occur. Buccal and lingual photographs were taken. Re-entry procedure; mesio-distal biopsy of the test and control sites; (6 dogs). After achievement of general and local anesthesia, a radiographic evaluation was executed. A full block section of the mandible was taken, placed into a sterile container with 10% formalin solution and evaluated histologically.

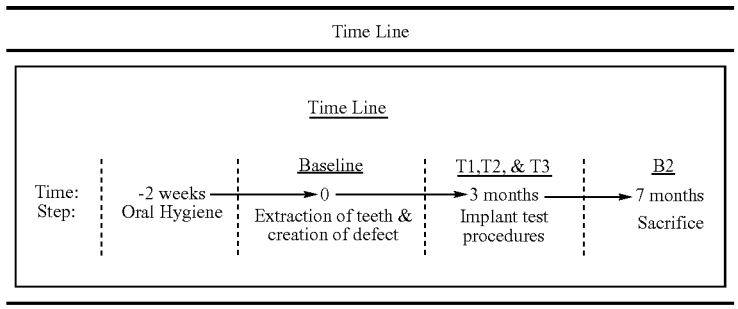

Results

Both groups receiving rhPDGF exhibited better soft tissue and also hard tissue healing when compared to the other test group without rhPDGF. Clinically and radiographically significant amounts of vertical ridge augmentation was achieved in 7 of 8 sites that received PDGF whereas only 1 of 4 sites had significant bone regeneration in the absence of PDGF. (FIGS. 1 to 3 provide a summary of the radiographic results obtained for the three treatment groups.) The soft tissues healed uneventfully in all but one site that received PDGF. In contrast, all but one site experienced soft tissue dehiscenses and infection in the absence of PDGF. The presence of the membrane did not appear to improve the outcome. That is, PDGF exhibited beneficial effects even in the absence of a membrane. Thus, the use of PDGF appears to eliminate the need to perform GBR.

The combination of rhPDGF and the deproteinized bone block and the presence or absence of a resorbable membrane is useful for treating defects in bone, particularly in the mandible or maxilla, and provides a means to augment the vertical ridge for insertion of metallic implants.

EXAMPLE 2

Sinus Elevation to Stimulate Bone Formation in a Maxillary Osseous Defect

The objective of this study was to evaluate the clinical utility of rhPDGF-BB in combination with β-TCP or other approved bone void filling matrices, for voids or gaps in the maxilla or mandible that are not intrinsic to the stability of the bony structure in accordance with standard clinical practice which included the use of ancillary bone augmentation materials.

Dosage and Method of Administration: All treatment kits contained 0.25 gm of (β-TCP (250-1000 micron particle size) and 0.5 mL sodium acetate buffer solution containing either 0.3 mg/mL rhPDGF-BB (Group I), or 1.0 mg/mL rhPDGF-BB (Group II). Following proper preparation of the surgical site, to receive the PDGF enhanced matrix, the solution was mixed with the β-TCP or other approved bone void filler(s) in a sterile container, such that the graft material was fully saturated. The hydrated graft was carefully packed into the osseous defect. In some cases the filled defect was covered with a resorbable collagen barrier membrane as commonly performed with periodontal surgeries. The tissue flaps were then replaced and secured with interdental sutures to achieve complete coverage of the surgical site.

Summary of Safety Results; There were no device related adverse events or serious adverse events experienced during the study. One subject was discontinued from the study due to non-compliance. No subject discontinued participation in the study due to an adverse event. The safety analysis did not identify any increased safety risk for either concentration of rhPDGF-BB with any of the approved matrices.

Summary of Performance Results: The effectiveness and safety outcomes of GEM 21S therapy were confirmed by the investigator's clinical utility assessments. Improvement in clinical attachment level, periodontal probing depth (PD) and bone fill (>3 mm) was seen in both treatment groups at 6 months post-periodontal surgery. The study results found that 100% of the patients in both rhPDGF-BB treatment groups exhibited an "excellent" outcome. In summary, rhPDGF-BB in combination with approved bone void filling matrices was shown to achieve clinical and radiographic effectiveness in patients six months post-surgery for the treatment of all types of defects, including: periodontal osseous defects, deficient maxillary alveolar ridge height, osseous defects associated with implants and extraction sockets. The use of ancillary bone grafting materials did not alter the benefits of the device of rhPDGF+β-TCP (also called GEM 21S (Biomimetic Therapeutics, Inc., Franklin, Tenn.).

Conclusions: It is concluded from this study that rhPDGF-BB in combination with β-TCP or other approved bone void filling matrices, for voids or gaps in the maxilla or mandible that are not intrinsic to the stability of the bony structure is a safe and clinically beneficial treatment modality for various oral and maxillofacial applications, including extraction sockets, sinus elevation, and ridge augmentation.

Discussion and Overall Conclusions: rhPDGF-BB (0.3 or 1.0 mg/ml) in combination with β-TCP was shown to be safe and clinically useful in this blinded bridging clinical trial (case series) in subjects with general bone defects. The clinical benefit of the treatment modalities was observed in all types of defects, including one, two and three wall defects, as well as circumferential defects. In addition, the materials used in the study were demonstrated to be clinically useful in extraction sockets, sinus elevations, ridge augmentations, and peri-implant defects. The study results demonstrated that rhPDGF-BB (0.3 or 1.0 mg/ml) in combination with β-TCP regenerated bone and soft tissue in the treatment of periodontal osseous defects, sinus elevation, implant and extraction socket. There were no adverse events attributable to the study device and the device was found to be safe.

It is concluded from this study that rhPDGF-BB (0.3 or 1.0 mg/ml) in combination with β-TCP is a safe and clinically beneficial treatment modality for a wide range of oral and maxillofacial applications, including extraction sockets, sinus elevation, and ridge augmentation. In addition rhPDGF-BB (0.3 or 1.0 mg/ml) was shown to be compatible with grafting materials such as xenografts, allografts, and/or bioresorbable guided tissue regeneration (GTR) membranes.

Sinus Elevation Studies

Subject 10-06 was treated for insufficient alveolar ridge height with a sinus augmentation procedure in the left posterior maxilla. A lateral window approach was utilized to place the graft of 0.3 mg/ml rhPDGF-BB in freeze dried bone allograft (FDBA) and xenograft (BioOss particulate material). Following placement of the graft, a collagen barrier membrane was placed over the lateral access window. The soft tissue flap was closed primarily with sutures and study medication containment within the treatment site, and soft tissue closure, were rated excellent by the investigator. Soft tissue healing was rated as excellent at all follow-up visits. Sutures were removed one week post-surgery. Radiographs obtained at 2 and 6 months post-surgery demonstrated normal healing with no sign of pathology. Additionally, histologic evaluation of a bone core sample obtained 6 months post-surgical, at the time of implant surgery demonstrated graft particles in new bone with extensive osteoid and new bone bridging the graft particles. At 6 months post-surgery, clinical utility assessment of treatment outcome was rated by the investigator as excellent for efficacy, safety and overall assessment; patient compliance and patient acceptance were rated as good.

Subject 10-09 was treated for insufficient alveolar ridge height (bilateral) in the posterior maxilla. Treatment consisted of a sinus floor augmentation with 0.3 mg/ml rhPDGF-BB in FDBA and xenograft. Prior to flap closure a collagen barrier membrane was placed over the sinus "window". Study medication containment within the lesion and soft tissue closure were rated excellent by the investigator. Soft tissue healing was rated initially as good and then excellent from one month post-surgery throughout the six month observation period. Sutures were removed at 2 weeks post-surgery. A radiograph was obtained immediately post-surgery and 3 months post-surgery for the left side and demonstrated increased vertical bone height of the sinus floor. This subject failed to comply with follow-up Visits 6 and 7 (18 and 24 weeks post-surgery) and did not complete the study; therefore clinical utility assessment of treatment outcome was not rated.

Subject 10-05 presented for treatment of insufficient vertical bone height (near pneumatization of the sinus) in the posterior maxilla. Treatment consisted of a sinus augmentation procedure utilizing a lateral sinus approach. The deficient ridge was augmented with 1.0 mg/ml rhPDGF-BB in FDBA and xenograft. The lateral window was covered, prior to flap closure, with a collagen barrier membrane. Study medication containment within the lesion was rated excellent and soft tissue closure was rated as good by the investigator. Soft tissue healing was rated as excellent on follow-up visits except visit 3 which was rated as good. Sutures were removed 1 and 3 weeks post-surgery. Radiographs obtained at 3, 4, and 6 months post-surgery demonstrated increased vertical height of the sinus floor with no sign of pathology. Additionally, increased bone trabeculation within the grafted site was observed and may be indicative of bone maturation within the grafted region. Bone cores obtained from the grafted site at the time of implant surgery reveal extensive new bone formation throughout the site with graft particles surrounded by new bone and osteoid. Bridging of the particles by bone and/or osteoid was also observed throughout the augmented site. Six months post-surgery, clinical utility assessment of treatment outcome was rated as excellent for efficacy, safety, patient acceptance and overall assessment; patient compliance was rated as good.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A method of enhancing bone augmentation in a subject comprising applying a composition consisting of a biocompatible matrix having incorporated therein a solution consisting of platelet derived growth factor (PDGF) in a buffer to a site for desired bone augmentation in the subject;
wherein the biocompatible matrix consists of collagen and a porous calcium phosphate;
wherein the calcium phosphate consists of particles in a range of about 75 micron to about 5000 micron in size;
wherein the calcium phosphate comprises interconnected pores; and
wherein the biocompatible matrix is flowable, moldable and/or extrudable.

2. The method of claim 1, wherein the calcium phosphate consists of particles in a range of about 100 microns to about 5000 microns in size.

3. The method of claim 1, wherein the calcium phosphate consists of particles in a range of about 100 microns to about 300 microns in size.

4. The method of claim 1, wherein the calcium phosphate consists of particles in a range of about 250 microns to about 1000 microns in size.

5. The method of claim 1, wherein the calcium phosphate consists of particles in a range of about 1000 microns to about 2000 microns in size.

6. The method of claim 1, wherein the calcium phosphate is resorbable such that the calcium phosphate is resorbed within one year of being implanted.

7. The method of claim 1, wherein the calcium phosphate has a porosity that facilitates osteoinduction, osteoconduction, or osteoinduction and osteoconduction.

8. The method of claim 1, wherein the calcium phosphate has macroporosity.

9. The method of claim 1, wherein the calcium phosphate has a porosity greater than 25%.

10. The method of claim 1, wherein the calcium phosphate has a porosity greater than 50%.

11. The method of claim 1, wherein the calcium phosphate is β-tricalcium phosphate.

12. The method of claim 1, wherein the PDGF is recombinant PDGF.

13. The method of claim 12, wherein the recombinant PDGF comprises recombinant human PDGF-BB.

14. The method of claim 13, wherein the recombinant human PDGF-BB (rhPDGF-BB) comprises at least 65% intact rhPDGF-B.

15. The method of claim 1, wherein the solution consists of PDGF at a concentration in a range of about 0.01 mg/ml to about 10 mg/ml in a buffer.

16. The method of claim 1, wherein the solution consists of PDGF at a concentration in a range of about 0.05 mg/mL to about 5 mg/mL in a buffer.

17. The method of claim 1, wherein the solution consists of PDGF at a concentration in a range of about 0.1 mg/mL to about 1.0 mg/mL in a buffer.

18. The method of claim 1, wherein the solution consists of PDGF at a concentration of about 0.3 mg/mL in a buffer.

19. The method of claim 1, wherein the PDGF comprises PDGF-AA, PDGF-BB, PDGF-AB, PDGF-CC, PDGF-DD, or a derivative thereof.

20. The method of claim 1, wherein the PDGF comprises one or more fragments of the B chain, wherein the fragments are selected from the group consisting of: the amino acid sequences 1-31 (SEQ ID NO: 1), 1-32 (SEQ ID NO: 2), 33-108 (SEQ ID NO: 3), 33-109 (SEQ ID NO: 4), and 1-108 (SEQ ID NO: 5) of the B chain.

21. The method of claim 1, wherein the biocompatible matrix consists of collagen and a porous calcium phosphate, wherein the calcium phosphate consists of particles in a range of about 100 microns to about 5000 microns in size, wherein the calcium phosphate has a porosity greater than 25%, wherein the calcium phosphate is β-tricalcium phosphate, wherein the PDGF comprises recombinant human PDGF-BB, and wherein the solution consists of PDGF at a concentration in a range of about 0.01 mg/ml to about 10 mg/ml in a buffer.

22. The method of claim 21, wherein the PDGF is present in the solution at a concentration of about 0.1 to about 1.0 mg/ml.

23. The method of claim 21, wherein the PDGF is present in the solution at a concentration of about 0.3 mg/ml.

24. The method of claim 21, wherein the calcium phosphate consists of particles in a range of about 100 microns to about 300 microns in size.

25. The method of claim 21, wherein the calcium phosphate consists of particles in a range of about 250 microns to about 1000 microns in size.

26. The method of claim 21, wherein the calcium phosphate consists of particles in a range of about 1000 microns to about 2000 microns in size.

27. The method of claim 21, wherein the calcium phosphate has a porosity that facilitates osteoinduction, osteoconduction, or osteoinduction and osteoconduction.

28. The method of claim 1, further comprising administering a bisphosphonate to the subject.

29. The method of claim 1, wherein the site is a maxillofacial site and a maxillofacial bone is augmented.

30. The method of claim 29, wherein the maxillofacial site is an alveolar ridge, a bone defect, a wall of the maxillary sinus, or an extraction socket.

31. The method of claim 29, wherein the maxillofacial site is located in a maxilla or a mandible.

32. The method of claim 1, wherein the subject is diabetic.

33. The method of claim 1, wherein the subject is an osteoporotic subject.

34. The method of claim 1, wherein the subject is a smoker.

35. The method of claim 1, wherein the subject is a steroid user.

36. The method of claim 1, wherein the method facilitates achievement of a stable osseointegrated implant.

37. The method of claim 1, wherein the method comprises repair of an extraction socket.

38. The method of claim 1, further comprising covering the composition with a bioresorbable membrane.

39. The method of claim 38, wherein the bioresorbable membrane comprises collagen.

40. The method of claim 38 or 39, wherein the bioresorbable membrane comprises PDGF.

* * * * *

SEQUENCE LISTING

<160> NUMBER OF SEQ ID NOS: 6

<210> SEQ ID NO 1
<211> LENGTH: 31
<212> TYPE: PRT
<213> ORGANISM: Artificial Sequence
<220> FEATURE:
<223> OTHER INFORMATION: Synthetic Construct

<400> SEQUENCE: 1

Ser Leu Gly Ser Leu Thr Ile Ala Glu Pro Ala Met Ile Ala Glu Cys
 1               5                  10                  15

Lys Thr Arg Thr Glu Val Phe Glu Ile Ser Arg Arg Leu Ile Asp
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic Construct

<400> SEQUENCE: 2

Ser Leu Gly Ser Leu Thr Ile Ala Glu Pro Ala Met Ile Ala Glu Cys
 1               5                  10                  15

Lys Thr Arg Thr Glu Val Phe Glu Ile Ser Arg Arg Leu Ile Asp Arg
            20                  25                  30

<210> SEQ ID NO 3
<211> LENGTH: 76
<212> TYPE: PRT
<213> ORGANISM: Artificial Sequence
<220> FEATURE:
<223> OTHER INFORMATION: Synthetic Construct

<400> SEQUENCE: 3

Thr Asn Ala Asn Phe Leu Val Trp Pro Pro Cys Val Glu Val Gln Arg
 1               5                  10                  15

Cys Ser Gly Cys Cys Asn Asn Arg Asn Val Gln Cys Arg Pro Thr Gln
            20                  25                  30

Val Gln Leu Arg Pro Val Gln Val Arg Lys Ile Glu Ile Val Arg Lys
        35                  40                  45

Lys Pro Ile Phe Lys Lys Ala Thr Val Thr Leu Glu Asp His Leu Ala
    50                  55                  60

Cys Lys Cys Glu Thr Val Ala Ala Arg Pro Val
65                  70                  75

<210> SEQ ID NO 4
<211> LENGTH: 77
<212> TYPE: PRT
<213> ORGANISM: Artificial Sequence
<220> FEATURE:
<223> OTHER INFORMATION: Synthetic Construct

<400> SEQUENCE: 4

Thr Asn Ala Asn Phe Leu Val Trp Pro Pro Cys Val Glu Val Gln Arg
 1               5                  10                  15

Cys Ser Gly Cys Cys Asn Asn Arg Asn Val Gln Cys Arg Pro Thr Gln
            20                  25                  30

Val Gln Leu Arg Pro Val Gln Val Arg Lys Ile Glu Ile Val Arg Lys
        35                  40                  45

```
Lys Pro Ile Phe Lys Lys Ala Thr Val Thr Leu Glu Asp His Leu Ala
    50                  55                  60

Cys Lys Cys Glu Thr Val Ala Ala Ala Arg Pro Val Thr
65                  70                  75
```

<210> SEQ ID NO 5
<211> LENGTH: 108
<212> TYPE: PRT
<213> ORGANISM: Artificial Sequence
<220> FEATURE:
<223> OTHER INFORMATION: Synthetic Construct

<400> SEQUENCE: 5

```
Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
                20                  25                  30

Thr Asn Ala Asn Phe Leu Val Trp Pro Pro Cys Val Glu Val Gln Arg
            35                  40                  45

Cys Ser Gly Cys Cys Asn Asn Arg Asn Val Gln Cys Arg Pro Thr Gln
        50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val
            100                 105
```

<210> SEQ ID NO 6
<211> LENGTH: 109
<212> TYPE: PRT
<213> ORGANISM: Artificial Sequence
<220> FEATURE:
<223> OTHER INFORMATION: Synthetic Construct

<400> SEQUENCE: 6

```
Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
                20                  25                  30

Thr Asn Ala Asn Phe Leu Val Trp Pro Pro Cys Val Glu Val Gln Arg
            35                  40                  45

Cys Ser Gly Cys Cys Asn Asn Arg Asn Val Gln Cys Arg Pro Thr Gln
        50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
            100                 105
```